(12) United States Patent
Corradi et al.

(10) Patent No.: US 8,821,557 B2
(45) Date of Patent: Sep. 2, 2014

(54) SURGICAL FASTENER WITH PREDETERMINED RESORPTION RATE

(71) Applicant: Covidien LP, Mansfield, MA (US)

(72) Inventors: Ralph Robert Corradi, Guilford, CT (US); David N. Fowler, Cheshire, CT (US); Christopher J. Criscuolo, Branford, CT (US); Earl Zergiebel, Guilford, CT (US); Michael Bettuchi, Middletown, CT (US); Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/799,298

(22) Filed: Mar. 13, 2013

(65) Prior Publication Data

US 2013/0197591 A1     Aug. 1, 2013

Related U.S. Application Data

(63) Continuation of application No. 13/190,669, filed on Jul. 26, 2011, now Pat. No. 8,414,627, which is a
(Continued)

(51) Int. Cl.
*A61B 17/86* (2006.01)
*A61B 17/88* (2006.01)
(Continued)

(52) U.S. Cl.
CPC ............... *A61B 17/861* (2013.01); *A61B 17/08* (2013.01); *A61B 17/8883* (2013.01); *B25B 23/101* (2013.01); *A61B 17/864* (2013.01); *A61L 31/06* (2013.01); *A61B 2017/0648* (2013.01); *A61B 17/8891* (2013.01); *A61B 17/064* (2013.01); *A61B 17/862* (2013.01); *A61B 17/8635* (2013.01); *A61B 17/869* (2013.01); *B25B 23/065* (2013.01); *A61B 17/866* (2013.01); *A61L 31/148* (2013.01); *Y10S 606/916* (2013.01); *A61B 2017/00004* (2013.01); *B25B 13/481* (2013.01); *B25B 17/00* (2013.01)
USPC ............................................ 606/308; 606/916

(58) Field of Classification Search
USPC ........ 411/378–426; 606/60, 74, 75, 246–279, 606/300–331
See application file for complete search history.

(56) References Cited

U.S. PATENT DOCUMENTS 3,911,781 A    10/1975   Bappert
4,884,572 A    12/1989   Bays et al.
(Continued)

FOREIGN PATENT DOCUMENTS

EP      0834280     4/1998
EP      199037      4/2002
(Continued)

OTHER PUBLICATIONS

Extended European Search Report corresponding to EP 106008305, dated Nov. 28, 2006; (5 pages).

*Primary Examiner* — Christopher Beccia

(57) ABSTRACT

A resorbable screw fastener and a method of firing with an applicator capable of applying a surgical fastener to tissue in order to form tissue connection to secure objects to tissue, the fastener including a body portion having a helical thread, a head portion disposed at the proximal end of the body portion. The resorbable screw fastener is 100% resorbed in vivo during a period of time ranging from about 14 days to about one year after implantation.

20 Claims, 30 Drawing Sheets

(51) Int. Cl.
*B25B 23/10* (2006.01)
*A61L 31/06* (2006.01)
*B25B 23/06* (2006.01)
*A61L 31/14* (2006.01)
*B25B 13/48* (2006.01)
*B25B 17/00* (2006.01)
*A61B 17/08* (2006.01)
*A61B 17/064* (2006.01)
*A61B 17/00* (2006.01)

Related U.S. Application Data continuation of application No. 11/113,879, filed on Apr. 25, 2005, now Pat. No. 8,002,811, which is a continuation-in-part of application No. PCT/US2004/018702, filed on Jun. 14, 2004.

(60) Provisional application No. 60/478,352, filed on Jun. 13, 2003.

(56) References Cited

U.S. PATENT DOCUMENTS

| | | | |
|---|---|---|---|
| 4,976,715 A | 12/1990 | Bays et al. | |
| 5,169,400 A | 12/1992 | Muhling et al. | |
| 5,203,864 A | 4/1993 | Phillips | |
| 5,236,563 A | 8/1993 | Loh | |
| 5,354,292 A | 10/1994 | Braeuer et al. | |
| 5,475,063 A | 12/1995 | Kaplan et al. | |
| 5,522,917 A | 6/1996 | Honda et al. | |
| 5,725,529 A | 3/1998 | Nicholson et al. | |
| 5,728,116 A | 3/1998 | Rosenman | |
| 5,730,744 A | 3/1998 | Justin et al. | |
| 5,733,307 A * | 3/1998 | Dinsdale | 606/232 |
| 5,830,221 A | 11/1998 | Stein et al. | |
| 5,891,146 A | 4/1999 | Simon et al. | |
| 5,941,882 A | 8/1999 | Jammet et al. | |
| 5,971,985 A | 10/1999 | Carchidi et al. | |
| 6,030,162 A | 2/2000 | Huebner | |
| 6,096,060 A | 8/2000 | Fitts et al. | |
| 6,248,108 B1 | 6/2001 | Tormala et al. | |
| 6,379,356 B1 | 4/2002 | Jackson | |
| 6,383,187 B2 | 5/2002 | Tormala et al. | |
| 6,402,757 B1 | 6/2002 | Moore, III et al. | |
| 6,454,768 B1 | 9/2002 | Jackson | |
| 6,508,830 B2 | 1/2003 | Steiner | |
| 6,533,454 B1 | 3/2003 | Kaikkonen et al. | |
| 6,537,312 B2 | 3/2003 | Datta et al. | |
| 6,562,051 B1 | 5/2003 | Bolduc et al. | |
| 6,569,186 B1 | 5/2003 | Winters et al. | |
| 6,656,183 B2 | 12/2003 | Colleran et al. | |
| 6,726,689 B2 | 4/2004 | Jackson | |
| 6,755,836 B1 | 6/2004 | Lewis | |
| 6,840,953 B2 | 1/2005 | Martinek | |
| 6,916,333 B2 | 7/2005 | Schmieding et al. | |
| 7,070,601 B2 | 7/2006 | Culbert et al. | |
| 7,138,441 B1 | 11/2006 | Zhang | |
| 7,261,716 B2 | 8/2007 | Strobel et al. | |
| 7,285,121 B2 | 10/2007 | Braun et al. | |
| 7,582,107 B2 | 9/2009 | Trail et al. | |
| 7,811,312 B2 | 10/2010 | Stevens et al. | |
| 7,883,529 B2 | 2/2011 | Sinnott et al. | |
| 8,002,811 B2 | 8/2011 | Corradi et al. | |
| 2003/0105471 A1 | 6/2003 | Schlapfer et al. | |
| 2003/0125745 A1 | 7/2003 | Tseng et al. | |
| 2003/0144696 A1 * | 7/2003 | Sinnott et al. | 606/232 |
| 2003/0158555 A1 | 8/2003 | Sanders et al. | |
| 2004/0076924 A1 | 4/2004 | Kim | |
| 2004/0230195 A1 * | 11/2004 | Kaikkonen et al. | 606/72 |
| 2005/0136764 A1 | 6/2005 | Sherman et al. | |
| 2006/0217727 A1 | 9/2006 | Munro et al. | |

FOREIGN PATENT DOCUMENTS

| | | |
|---|---|---|
| EP | 2005975 | 12/2008 |
| WO | WO 98/11814 | 3/1998 |
| WO | WO 01/97677 | 12/2001 |
| WO | WO 02/091932 | 11/2002 |
| WO | WO 03/034925 | 5/2003 |
| WO | WO 2004/112841 | 12/2004 |

* cited by examiner

SURGICAL FASTENER WITH PREDETERMINED RESORPTION RATE

CROSS REFERENCE TO RELATED APPLICATIONS

This application is a Continuation of, and claims the benefit of and priority to, U.S. patent application Ser. No. 13/190,669 (U.S. Patent Publication Application No. 2011-0282401), filed on Jul. 26, 2011, which, in turn, is a Continuation of, and claims the benefit of and priority to, U.S. patent application Ser. No. 11/113,879 (U.S. Pat. No. 8,002,811), filed on Apr. 25, 2005, which, in turn, is a Continuation-in-Part of, and claims the benefit of and priority to, International Application PCT/US04/18702, filed on Jun. 14, 2004, which, in turn, claims the benefit and priority to U.S. Provisional Patent Application Ser. No. 60/478,352 filed on Jun. 13, 2003, the disclosures of each of which are hereby incorporated by reference herein.

BACKGROUND OF THE INVENTION

1. Technical Field

The present disclosure relates generally to surgical fasteners, surgical fastener appliers and methods for connecting body tissue and, more particularly, to bioresorbable screw fasteners, screw fastener appliers, and methods of using the screw fastener applier to fire multiple resorbable screw fasteners to a target surgical site.

2. Description of Related Art

Surgical fasteners are used to eliminate the need for suturing, which is often time consuming and inconvenient. Surgical fasteners accomplish in seconds what would have taken many minutes to accomplish by suturing, thus reducing operating time and trauma to the patient. In hernia repair procedures, for example, the weakened area of the abdominal wall may be reinforced with a synthetic mesh or by suturing the abdominal tissue. In such an instance, a surgical fastener may be used, in lieu of, or in addition to, a surgical suture to fix the position of the mesh.

For example, in some cases titanium staples are utilized to retain the mesh in place. These staples thus become permanent residents in the body cavity. Other fasteners may be utilized which are made of bioresorbable materials, many of which, however, remain in vivo for extended periods of time. A disadvantage of permanent metal staples and/or those that remain in the body for an extended period of time is the possibility of the formation of excessive scar tissue (adhesions), which in turn can cause further patient complications and hinder future surgical procedures. In addition, these permanent or long-term staples may be associated with increased discomfort to the patient over time as a result of the hernia repair procedure.

In view of the widespread use of surgical fasteners, a continuing need exists for improved surgical fasteners, surgical fastener appliers, and methods of applying the surgical fasteners.

SUMMARY

Accordingly, the present disclosure relates to a resorbable fastener to form tissue connections. Because it is resorbable, use of the fastener of the present disclosure reduces the amount of foreign material in the patient's body, thereby minimizing adhesion formation and reducing fastener-associated long-term discomfort to the patient. The fastener of the present disclosure retains sufficient strength for enough time to permit the healing and/or in-growth of tissue at the repair site, after which time it is completely resorbed by the body. The fastener of the present disclosure can be 100% resorbed in vivo during a period of time ranging from about 14 days to about one year after implantation.

In one embodiment, the fastener of the present disclosure has a shear strength of about 3.5 pounds to about 5.5 pounds during a period of time ranging from the time of implantation in vivo to about one week after implantation, a shear strength ranging from about 0.5 pounds to about 4.2 pounds during a period of time ranging from about one week to about 1.5 weeks after implantation, and a shear strength of about 0 pounds about one year after implantation.

In one embodiment, the resorbable fastener of the present disclosure is a screw fastener which possesses a head configuration which permits the use of a combined rotational force and linear force to facilitate insertion. The resorbable screw fastener is tacked into body tissue to form tissue connection to secure objects such as a mesh material to tissue.

In another embodiment, the resorbable fastener is a screw fastener which includes a body portion having a helical thread, a head portion disposed at the proximal end of the body portion and a blunt end at a distal portion of the body portion. The head portion includes a driver receiving configuration on its outer diameter, said driver receiving configuration is used to transmit both linear and rotational forces in order to drive the resorbable screw fastener. The body portion of the bioresorbable fastener is threaded, with the spacing between adjacent threads being augmented to provide a wider pitch. In addition, the thread's outer diameter is enlarged creating substantially more land, giving the resorbable screw fastener greater stability and preventing dislodgement from the body tissue. The resorbable screw fastener includes a cannulated center lumen with an opening extending from the head portion through the longitudinal length of the body portion of the resorbable fastener. The head portion may also include a flat segment, which may further extend to the outside of the threads.

In other embodiments, the fastener of the present disclosure may possess a helical configuration. In yet another embodiment, the fastener of the present disclosure may be a clip.

Other features and advantages of the present invention will become apparent from the following detailed description, taken in conjunction with the accompanying drawings, which illustrate, by way of example, the principals of the invention.

BRIEF DESCRIPTION OF THE DRAWINGS

Embodiments of the present disclosure will be better appreciated by reference to the drawings wherein:

FIG. 47 is a plan view, on an enlarged scale, FIG. 48 is a side view;

DETAILED DESCRIPTION OF THE EMBODIMENTS

Figure 2:
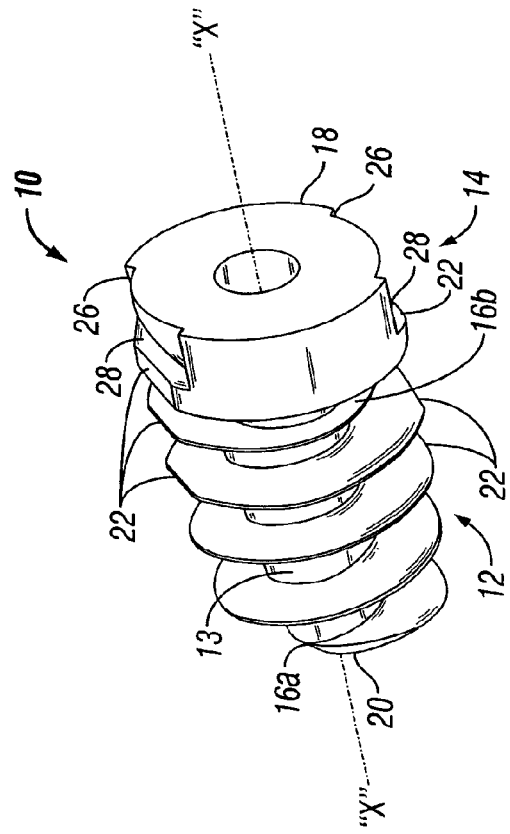
FIG. 2 is another perspective view of the resorbable screw fastener of FIG. 1.

A resorbable surgical fastener is provided which may be utilized to attach an object to tissue or to attach tissue to tissue, such as tissue to ligament. The resorbable surgical fastener permits tissue healing and in-growth and degrades in vivo after sufficient healing and/or in-growth has occurred, but prior to the formation of adhesions, thereby minimizing any pain or discomfort which can occur through the placement of permanent surgical fasteners or surgical fasteners which remain in vivo for extended periods of time.

Referring now in detail to the figures, which are included for purposes of illustration and not by way of limitation, a resorbable fastener of the present disclosure is illustrated in FIGS. 1-4, and is designated generally as resorbable screw fastener 10.

The presently disclosed embodiments of resorbable screw fastener 10 contemplate the insertion of a resorbable screw fastener through a trocar into various tissue types using minimal application of force. Tissue typically wicks into the mesh in about 7-10 days, meaning that the fastener must maintain a certain structural integrity for at least that amount of time. In some embodiments, resorbable screw fastener 10 may be constructed so as to maintain its structural strength by about 80% for about 10-21 days. Thereafter, the tissue will grow into the mesh and the resorbable screw fastener 10 will be resorbed by the body at a fixed rate leaving in place only the mesh.

Although the specific focus of this disclosure will be on a laparoscopic hernia repair, it will be noted that hernia repair is merely representative of a type of surgical procedure wherein resorbable screw fastener 10 can be utilized. Other such procedures include vaginal prolapse repair, use of an anchored mesh for urinary incontinence repair, etc.

In the following description, as is traditional, the term "proximal" refers to the portion of the screw, applier or instrument closest to the operator, while the term "distal" refers to the portion of the screw, applier or instrument remote from the operator.

Referring now to FIGS. 1-4, resorbable screw fastener 10 includes two main components, namely a body portion 12 defining a longitudinal axis "X" and a substantially circular head portion 14 disposed on a proximal end of body portion 12. Resorbable screw fastener 10 further includes a central cannulated opening or lumen 18 extending along the longitudinal "X" axis of body portion 12 and head portion 14 for receiving a mating part therein, as will be described in greater detailed below. In one embodiment, cannulated lumen 18 has a hexagonal traverse cross-sectional profile (not shown). Alternatively, it is envisioned that cannulated lumen 18 may have a circular, rectangular or triangular traverse cross-sectional profile.

Body portion 12 includes a helical thread 16 extending along a length thereof, and may also include a truncated or blunt distal end 20. Further body portion 12 includes a center shaft 13 extending along a length thereof. Center shaft 13 and/or may have a constant outer distance D1 and D2, or may taper from a larger proximal end to a smaller distal end.

In one embodiment, head portion 14 has a distance "D" (of about 3.51 mm) which is approximately 54% of an overall length "L" (of about 6.5278 mm) of screw fastener 10. Additionally, body portion 12 has a length "L1" which is approximately 70-80% of the overall length "L" of screw fastener 10. In another embodiment, length "L1" is about 77% of the overall length "L". For example, head portion 14 may have a height or length "L2" of about 1.5 mm and body portion 12 may have a length "L1" of about 5.0 mm. In yet another embodiment, distance "D" of head portion 14 is substantially equal to an outer distance "D1" of body portion 12 and helical thread 16.

The dimensions and physical characteristics of resorbable screw fastener 10 are selected to insure a secure attachment of screw fastener 10 to tissue. Similarly, the dimensions and physical characteristics of applicator 100 (FIG. 5) utilized to dispense screw fastener 10 into tissue are dependent upon the particular application.

With continued reference to FIGS. 1-4, head portion 14 includes driver receiving recesses or structure, in the form of slots 28, formed in an outer radial surface of head portion 14. Slots 28 are configured to transmit torque to screw fastener 10. In one embodiment, a pair of diametrically opposed slots 28 are formed in head portion 14. Additionally, each slot 28 may be tapered at an angle toward the longitudinal "X" axis extending distally from a proximal surface head portion 14. The taper of slots 28 helps to facilitates rotation and driving of screw fastener 10. Alternatively or additionally, it is envisioned that a torque transmitting feature may be provided on slots 28, in the form of shoulders 26, or on the centrally cannulated opening 18, in the form of a keyed surface (not shown). As described herein, the torque transmitting feature allows for screw fastener 10 to be rotated.

Figure 1:
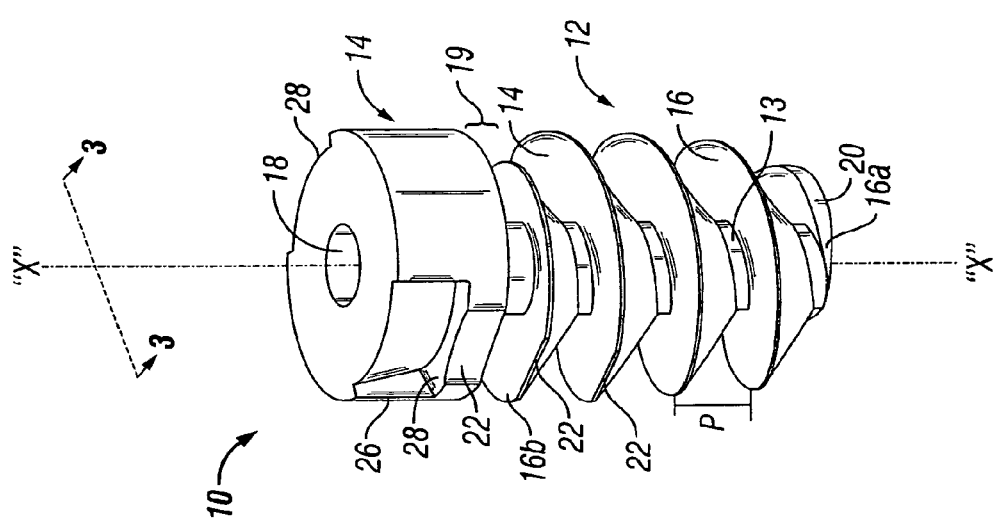
FIG. 1 is a perspective view of a resorbable fastener in accordance with an embodiment of the present disclosure.
Figure 4:
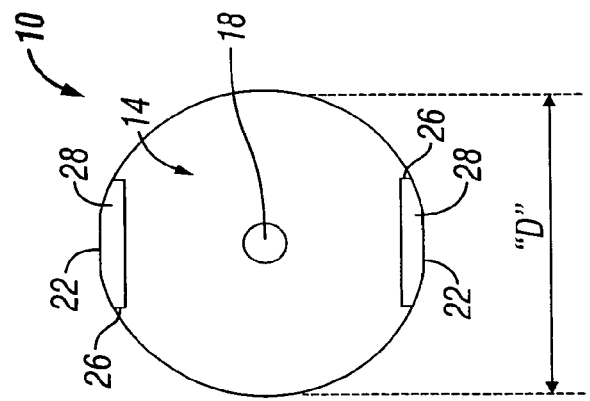
FIG. 4 is an orthogonal top view of the resorbable screw fastener of FIG. 3.
Figure 3:
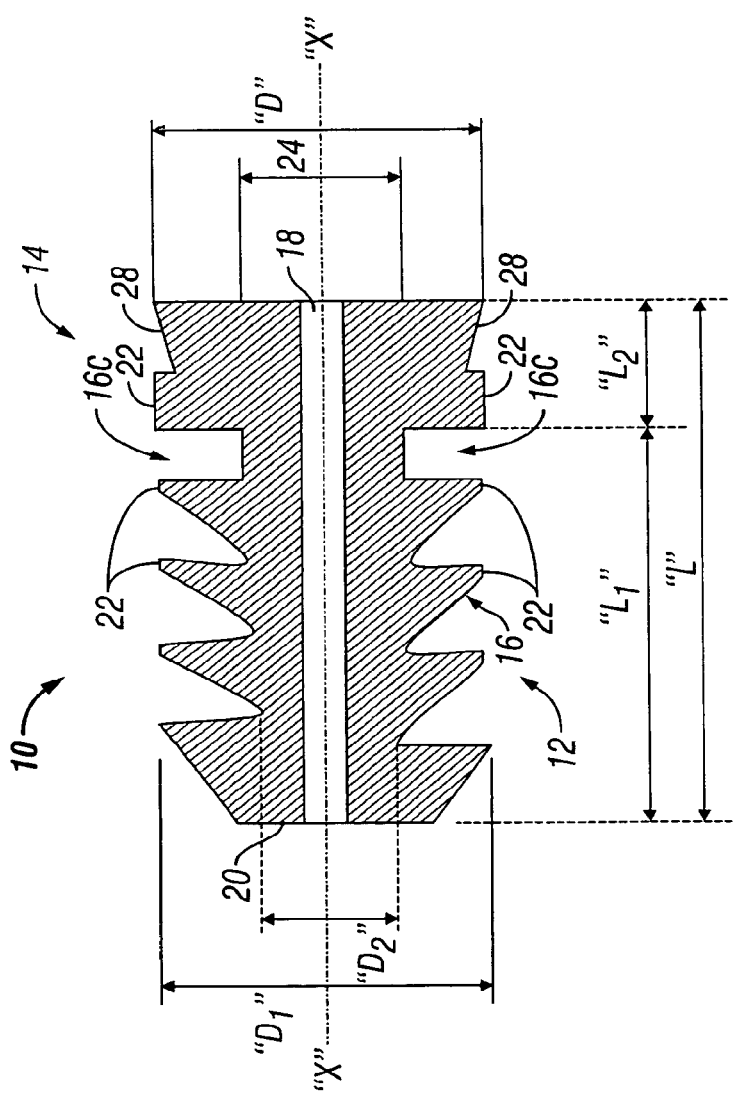
FIG. 3 is a longitudinal cross-sectional view of the resorbable screw fastener of FIG. 1 taken along line 3-3 of FIG. 1.

With particular reference to FIG. 3, body portion 12 includes a single continuous helical thread 16 thereon. Thread 16 includes an outer distance "D1" which is substantially enlarged as compared to an inner distance "D2" thereof. Having a substantially enlarged outer distance "D1" as compared to inner distance "D2" enables the tissue to more fully and intimately adhere to the surface of screw fastener 10, consequently reducing instances of dislodgement of screw fastener 10. Thread 16 has a pitch "P" (as seen in FIG. 1) between adjacent individual threads.

Thread 16 is also desirably tapered at both a distal lead-in 16a and a proximal run-out 16b. A space or gap 16c is provided between proximal thread run-out 16b and a distal surface of head portion 14. Gap 16c allows for the surgical mesh to rest therein. It is envisioned that the pitch of thread 16 may be larger or smaller depending on the particular surgical procedure. Additionally, the cross-sectional shape of thread 16 may be triangular, rectangular, etc.

As seen in FIGS. 1-4, screw fastener 10 may include at least one pair (three pairs shown) of diametrically opposed planer or flattened surfaces 22 formed in the outer radial surface of head portion 14 and helical thread 16. Each planar surface 22 may additionally be in radial registration with a respective slot 28. Planar surface 22 extends distally from head portion 14 to helical thread 16 of body portion 12 and substantially along the entire length of body portion 12. Planar surface 22 is provided for orientation of screw fastener 10 inside fastener applier 100, as will be described in detail below. It is envisioned that other features may be provided for orientation of screw fastener 10 inside fastener applier 100.

Screw fasteners 10 may be fabricated from any bioresorbable polymer or copolymer known to those skilled in the art, so long as the polymer utilized has sufficient strength and possesses the necessary mechanical properties to permit its formation into a screw fastener of the present disclosure and the application thereof. Suitable polymers which may be utilized to form screw fasteners 10 include, but are not limited to, trimethylene carbonate, caprolactone, dioxanone, glycolic acid, lactic acid, glycolide, lactide, homopolymers thereof, copolymers thereof, and combinations thereof.

In one embodiment, the fastener of the present disclosure may be made of a glycolide-lactide copolymer. The amount of glycolide can range from about 10% (mole percent) to about 50% of the glycolide-lactide copolymer utilized to form the fastener of the present disclosure, typically from about 15% to about 45% of the glycolide-lactide copolymer. The amount of lactide can thus range from about 90% (mole percent) to about 50% of the glycolide-lactide copolymer utilized to form the fastener of the present disclosure, typically from about 85% to about 55% of the glycolide-lactide copolymer. In another embodiment, a fastener of the present disclosure may be a homopolymer of glycolic acid (100% polyglycolide).

In yet another embodiment, the fastener of the present disclosure may be made of a glycolide-trimethylene carbonate copolymer. The amount of glycolide can range from about 50% (mole percent) to about 90% of the glycolide-trimethylene carbonate copolymer utilized to form the fastener of the present disclosure, typically from about 55% to about 70% of the glycolide-trimethylene carbonate copolymer. The amount of trimethylene carbonate can thus range from about 10% (mole percent) to about 50% of the glycolide-trimethylene carbonate copolymer utilized to form the fastener of the present disclosure, typically from about 30% to about 45% of the glycolide-trimethylene carbonate copolymer.

In other embodiments, screw fastener 10 may be made of polyglycolic acid or poly-glycolide (PGA) and/or polylactic acid (PLA), any other biocompatible implantable material, or any combinations thereof.

In some particularly useful embodiments screw fastener 10 may be fabricated from a medical bioresorbable copolymer material including, but not limited to, a polyglycolide -co-L-lactide at a ratio of 18/82, a polyglycolide-co-L-lactide at a ratio of 42/58, or a polyglycolide-co-trimethylene carbonate at a ratio of 63/37.

The copolymers described herein can be produced utilizing methods known to those skilled in the art. In some embodiments, the polymerization may include use of a catalyst (e.g., stannous octoate) and/or an initiator (e.g., glycolic acid). In addition, in some instances additives and/or fillers may be added to the screw fasteners of the present disclosure. For example, screw fastener 10, or a portion thereof, may be coated with a biocompatible material such as parylene, that may also be lubricious, which provides for easier delivery of screw fastener 10 into tissue. In addition, a parylene coating may extend the resorption time of screw fastener 10. Typically, such screw fasteners 10 are formed using an injection molding process as would be understood by one skilled in the art.

Screw fasteners 10 fabricated from a bioresorbable material in accordance with the present disclosure maintain their structural integrity after implantation (e.g., about 80% of original strength) for a predetermined period of time, depending on the characteristics of the particular copolymer used. Such characteristics include, for example, the components of the copolymer, including both the monomers utilized to form the copolymer and any additives thereto, as well as the processing conditions (e.g., rate of copolymerization reaction, temperature for reaction, pressure, etc.), and any further treatment of the resulting copolymers, i.e., sterilization, etc.

Screw fasteners 10 of the present disclosure typically maintain their structural integrity, i.e., 80% of their original strength, after implantation for periods of time ranging approximately from about 5 days to about 52 weeks, typically from about 7 days to about 90 days, more typically from about 10 days to about 21 days.

The screw fasteners 10 of the present disclosure are typically resorbed in vivo within one year of implantation in a patient's body. As with maintenance of the structural integrity of the screw fastener discussed above, the rate of resorption of the screw fasteners may also depend on the characteristics of the particular copolymer used (including both the monomers utilized to form the copolymer and any additives thereto), as well as the processing conditions (e.g., rate of copolymerization reaction, temperature for reaction, pressure, etc.), and any further treatment of the resulting copolymers, i.e., sterilization, etc. As noted above, the addition of a parylene coating may, in some embodiments, extend the resorption time of screw fastener 10 so that it takes a longer time to be resorbed by a subject patient's body.

Typically, the screw fasteners 10 of the present disclosure are not 100% resorbed before the expiration of one week post-implantation in a subject, but are 100% resorbed by the body of a subject patient after implantation within one year, typically less than 9 months, more typically less than 6 months, in some cases less than 3 months. Thus, in some embodiments, the screw fastener 10 may be 100% resorbed in a subject patient within about 14 days to about one year after implantation of screw fastener 10, typically from about 21 days to about 3 months after implantation, more typically from about 28 days to about 2 months after implantation.

It has been found that repair of, for instance, a hernia requires that the mesh be anchored using fasteners capable of withstanding certain forces exerted upon it, as for instance that may be experienced when a patient coughs or lifts a heavy load. For this reason, the fastener of the present disclosure has been designed to withstand a tensile load of from about 0 to about 10 pounds of force, typically from about 2 to about 8 pounds of force upon implantation, and a shear load of about 0 to about 5.5 pounds of force, typically from about 3.5 to about 4.4 pounds of force upon implantation.

Conversely, it has also been found that fasteners capable of withstanding such forces for indefinite periods of time result in the formation of adhesions in a patient and increased pain and patient discomfort. The fasteners of the present disclosure have therefore been designed with these requirements of strength while requiring that the fastener be totally resorbed by the body within a certain period of time so as to minimize such adverse implications to the patient.

In one particularly useful embodiment, fasteners of the present disclosure are capable of maintaining a shear load for a desired period of time, after which the shear load begins to decrease. As used herein, the term "shear load" is synonymous with "shear strength" and the two may be used interchangeably. From the time of implantation in vivo to about one week after implantation, the fasteners of the present disclosure generally possess a shear strength ranging from about 3.5 pounds to about 5.5 pounds, typically from about 3.8 pounds to about 4.2 pounds. From about 1 week to about 1.5 weeks post-implantation, the shear strength ranges from about 0.5 pounds to about 4.2 pounds, typically from about 0.65 pounds to about 2.5 pounds, more typically from about 0.75 pounds to about 1.5 pounds and, eventually, a fastener of the present disclosure will have a shear strength of about 0 pounds about one year post-implantation. In some embodiments the fastener of the present disclosure may have a shear strength of about 0 pounds at a time ranging from about 3 weeks to about 12 weeks post-implantation, typically at a time of from about 4 weeks to about 8 weeks post-implantation.

Figure 39:
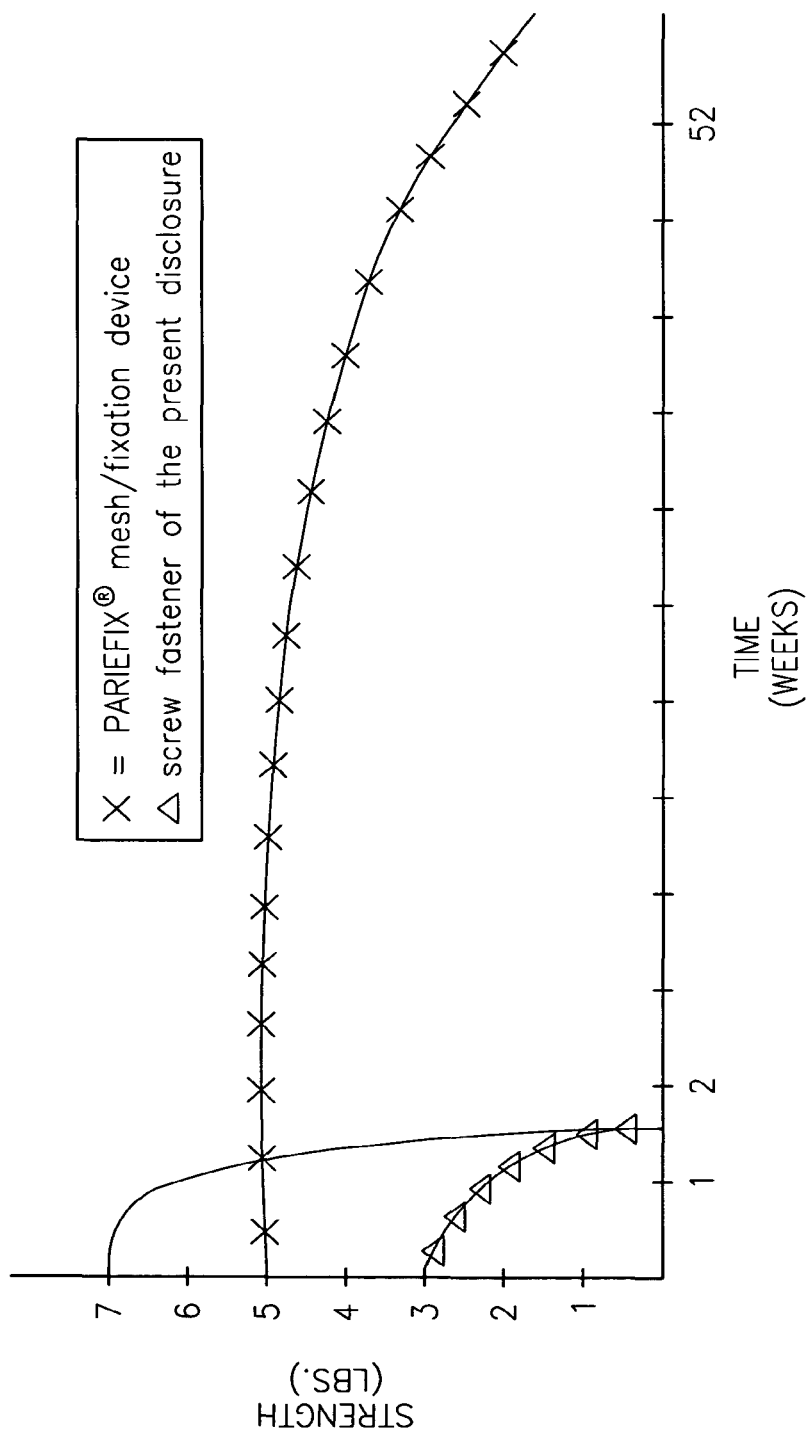
FIG. 39 is a graph depicting the strength-loss profile of a resorbable fastener of the present disclosure compared with a commercially available fastener.

FIG. 39 is a graph comparing the loss of strength of one suture fastener of the present disclosure with a commercially available fixation device (a PARIEFIX® mesh/fixation device commercially available from Sofradim Corp. (Wrentham, Mass.)). The fastener was made of a 18/82 polyglycolide-co-L-lactide copolymer. As can be seen in FIG. 39, in this embodiment, the fastener of the present disclosure should have an initial strength capable of withstanding at least 3.5 pounds of force in any direction upon implantation (at time=0), which remains for about 7 days, at which point the fastener may begin to lose strength. At that point, the resorption of the screw fastener 10 of the present disclosure will continue until it is 100% resorbed by the body. As noted above, the screw fastener 10 of the present disclosure is typically 100% resorbed in less than one year after implantation. To the contrary, the PARIEFIX® mesh/fixation device maintains an ability to withstand about 5 pounds of force for more than one year, which is not necessary in the repair of a hernia utilizing a hernia mesh and requires the surgical fastener to remain in vivo for an extended period of time, i.e., at least for more than one year, which could lead to the formation of adhesions in a patient and increased pain and patient discomfort.

Figure 40:
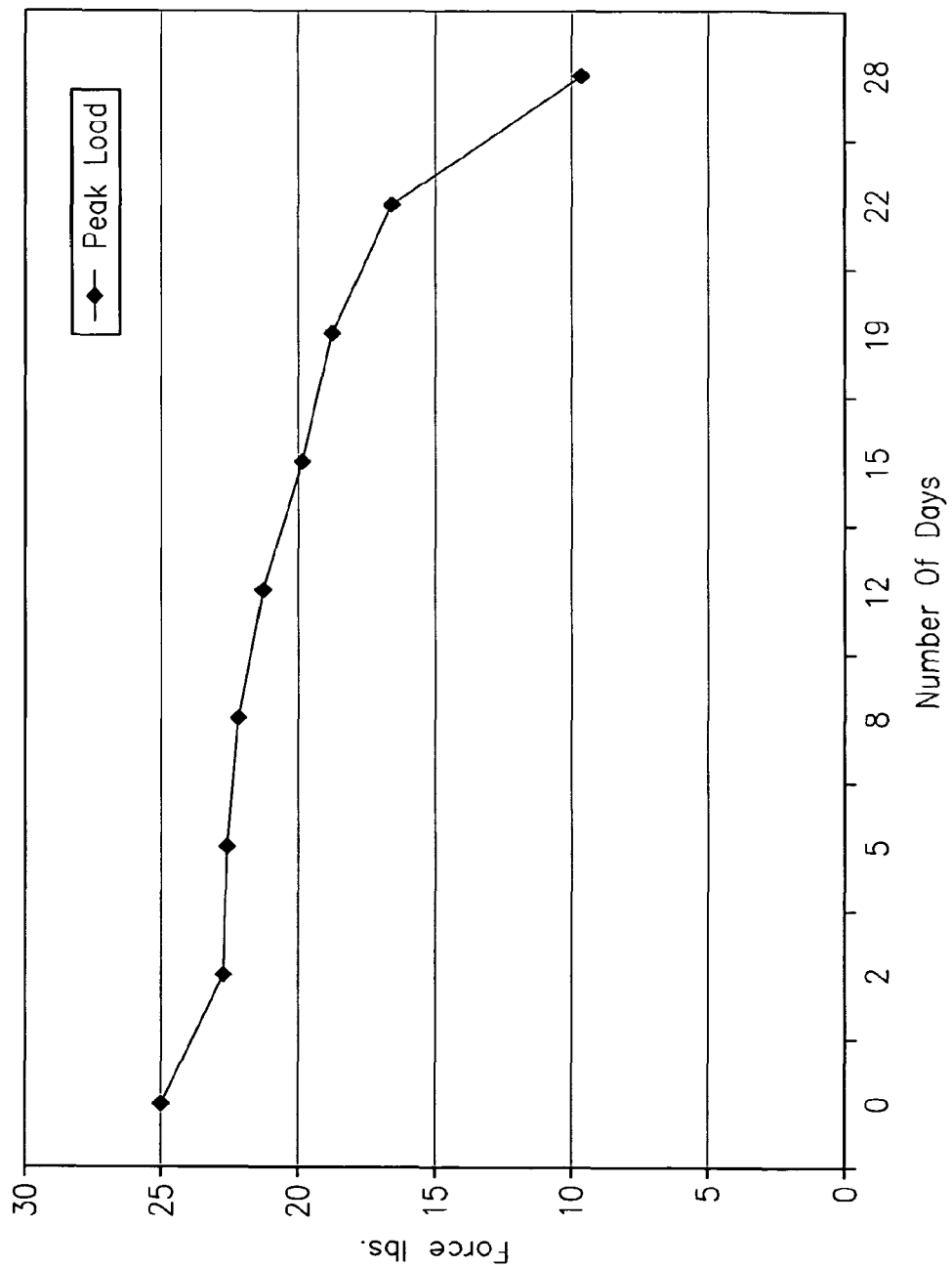
FIG. 40 is a graph depicting tensile test results of a fastener of the present disclosure affixed to a synthetic dog bone made of a glycolide-lactide copolymer.
Figure 41:
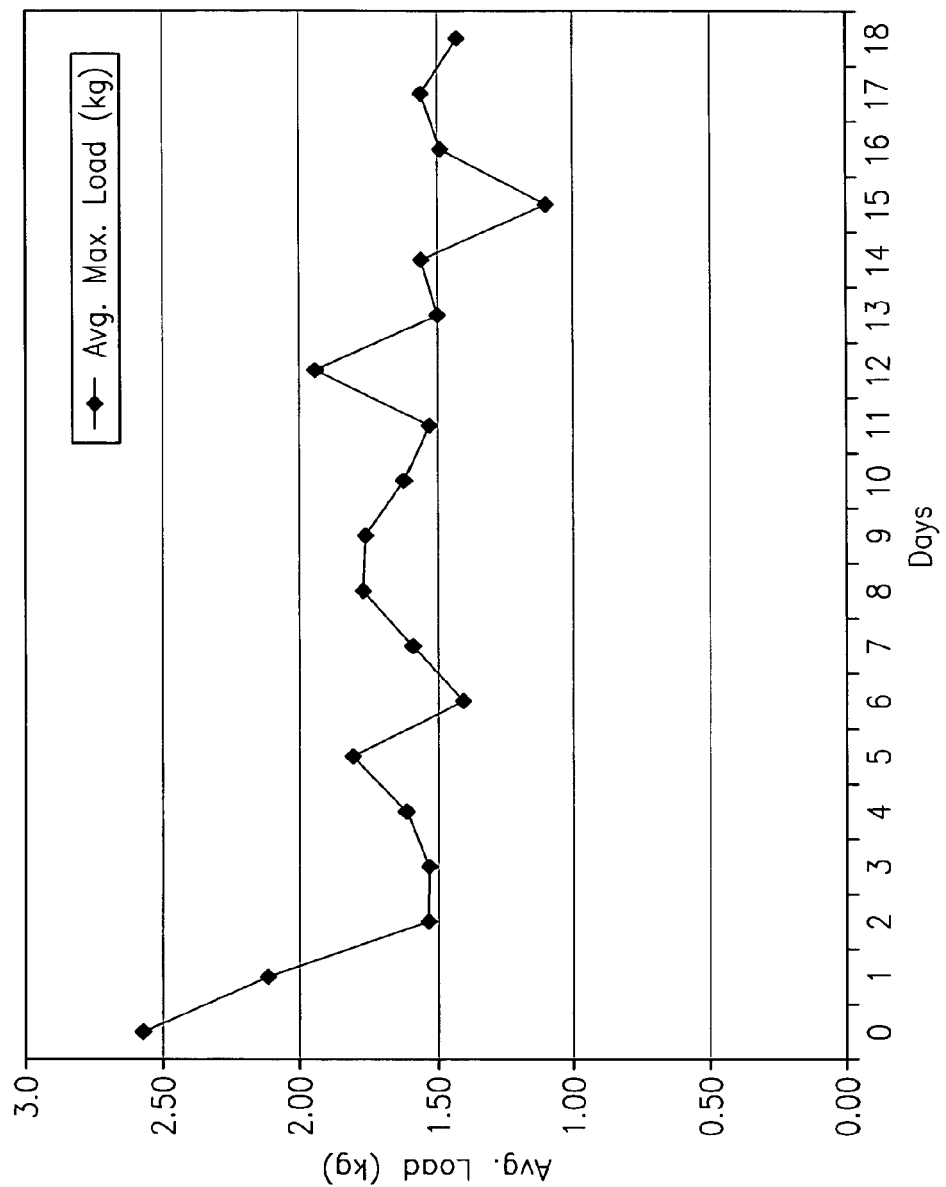
FIG. 41 is a graph depicting shear test results of a fastener of the present disclosure affixed to a synthetic dog bone made of a glycolide-lactide copolymer.

ASME dogbones and fasteners were created out of 18/82 polyglycolide-co-L-lactide copolymer. Under an Instron load, at day zero the dogbone was either subjected to a tensile load or the fastener was subjected to a shear load. The dogbones and fasteners tested after day zero were placed in a saline bath simulating an in vivo environment. Depending on the day intervals, subsequent dogbones and fasteners were removed from the saline bath and tested the same way as on day zero. FIG. 40 shows a graph of tensile results for a synthetic dog bone made of an 18/82 polyglycolide-co-L-lactide copolymer. As can be seen in FIG. 40, the synthetic dog bone had a peak load of about 25 lbs. upon placement in the saline bath, which corresponded to implantation, which decreased to below 10 pounds at 28 days post-implantation, i.e., after placement in the bath. The fastener made with this same material was subjected to shear testing. FIG. 41 is a graph showing the shear test results. As can be seen in FIG. 41, the average load for these fasteners ranged from slightly more than 2.50 kgf (5.51 lbs) upon implantation and decreased to below 1.50 kgf (3.31 lbs) at 18 days post-implantation.

In some embodiments, it may be desirable to treat the fasteners of the present disclosure to control their rate of degradation. For example, in some embodiments it may be desirable to heat the fasteners of the present disclosure to obtain the desired rate of resorption. The heating of the fastener may also remove monomers remaining in the polymers utilized to form the fasteners. Suitable temperature for heating the fasteners can range from about 100° C. to about 160° C., typically from about 120° C. to about 143° C., for a period of time ranging from about 2 hours to about 24 hours, typically from about 8 hours to about 16 hours. In some embodiments, the heating may take place in a vacuum.

Figure 49:
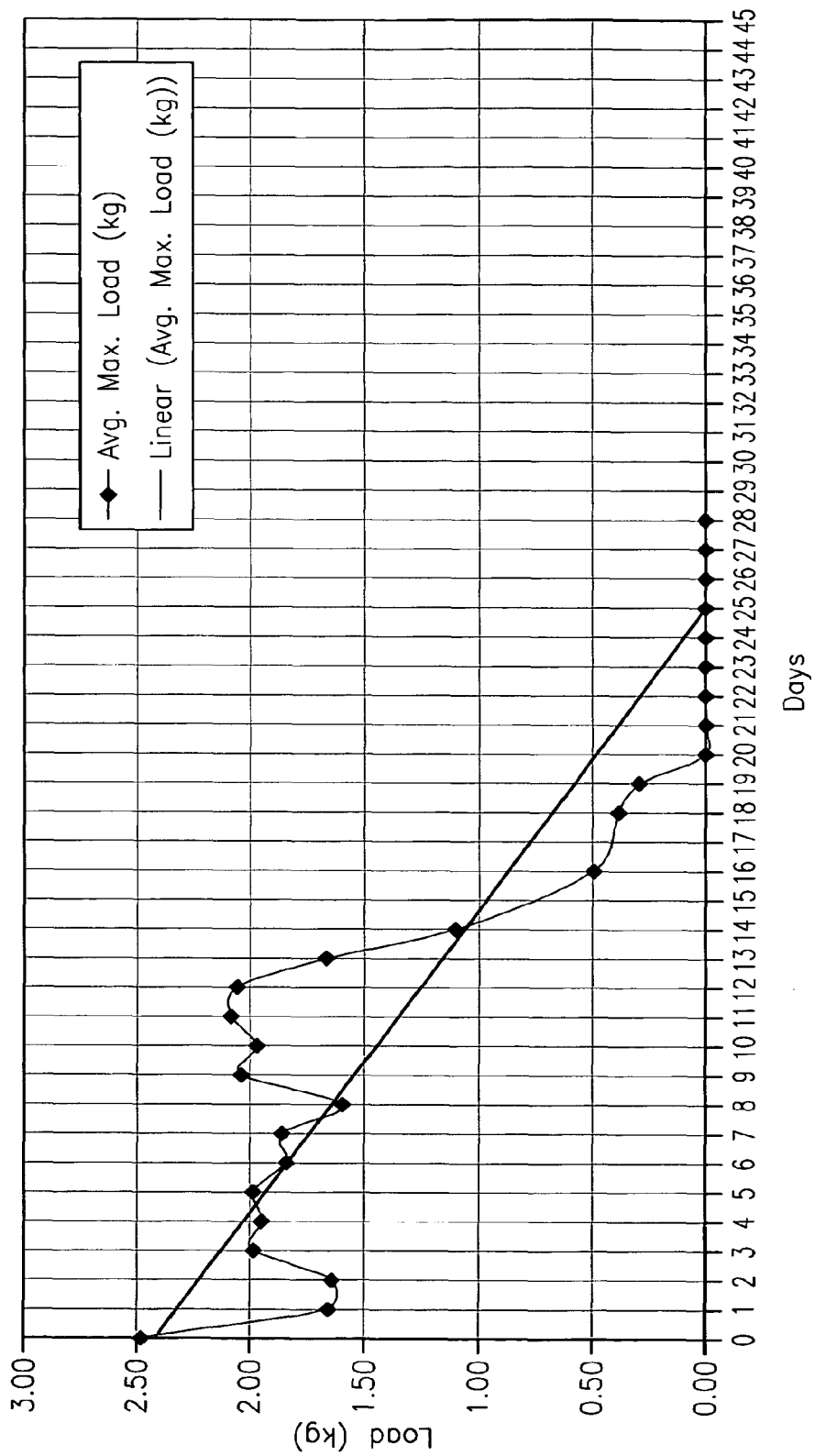
FIG. 49 is a graph depicting the reduction in the maximum load for a fastener of the present disclosure made of a glycolide-lactide copolymer that had been subjected to heating.

FIG. 49 is a graph depicting the maximum load for fasteners of the present disclosure that were subjected to heat treatment. The fasteners were made of a homopolymer of glycolic acid (100% polyglycolide). Fasteners were heat treated in a vacuum to 143° C. for 12 hours to determine the absorption rate for the desired fastener form. A shear force test was conducted after the fasteners were placed in a saline bath simulating an in vivo environment, the results of which are set forth in FIG. 49. As can be seen in FIG. 49, the day zero strength was 2.50 kgf (5.51 lbs), while the day thirteen strength was 1.66 kgf (3.66 lbs). At day fourteen and subsequent days, the strength dropped sharply.

In other embodiments, the rate of degradation of the fasteners of the present disclosure may be controlled by exposing them to a low-temperature gas plasma at a pressure substantially below atmospheric for a sufficient period of time. Such a method of treatment is known and includes, for example, the treatment disclosed in U.S. Pat. No. 5,236,563, the entire disclosure of which is incorporated by reference herein. Typically, the surface treatment is limited in time to treat the surface layer to a depth from about 100 to about 1500 Angstroms, thereby producing a cross-linked polymer layer that will not adversely affect the desired handling qualities of the polymer.

Fasteners treated with such a gas plasma have a thin surface layer possessing additional cross-links of the polymer and/or an increase in the surface hydrophobicity of the polymer, which results from a reaction of the polymer with surface-modifying components, typically halogens such as fluoride ions. The treated polymers possess desirable degradation characteristics including wettability and fluid diffusivity, so as to modulate the hydrolyzation rate of the polymer utilized to make the fastener of the present disclosure.

Figure 50:
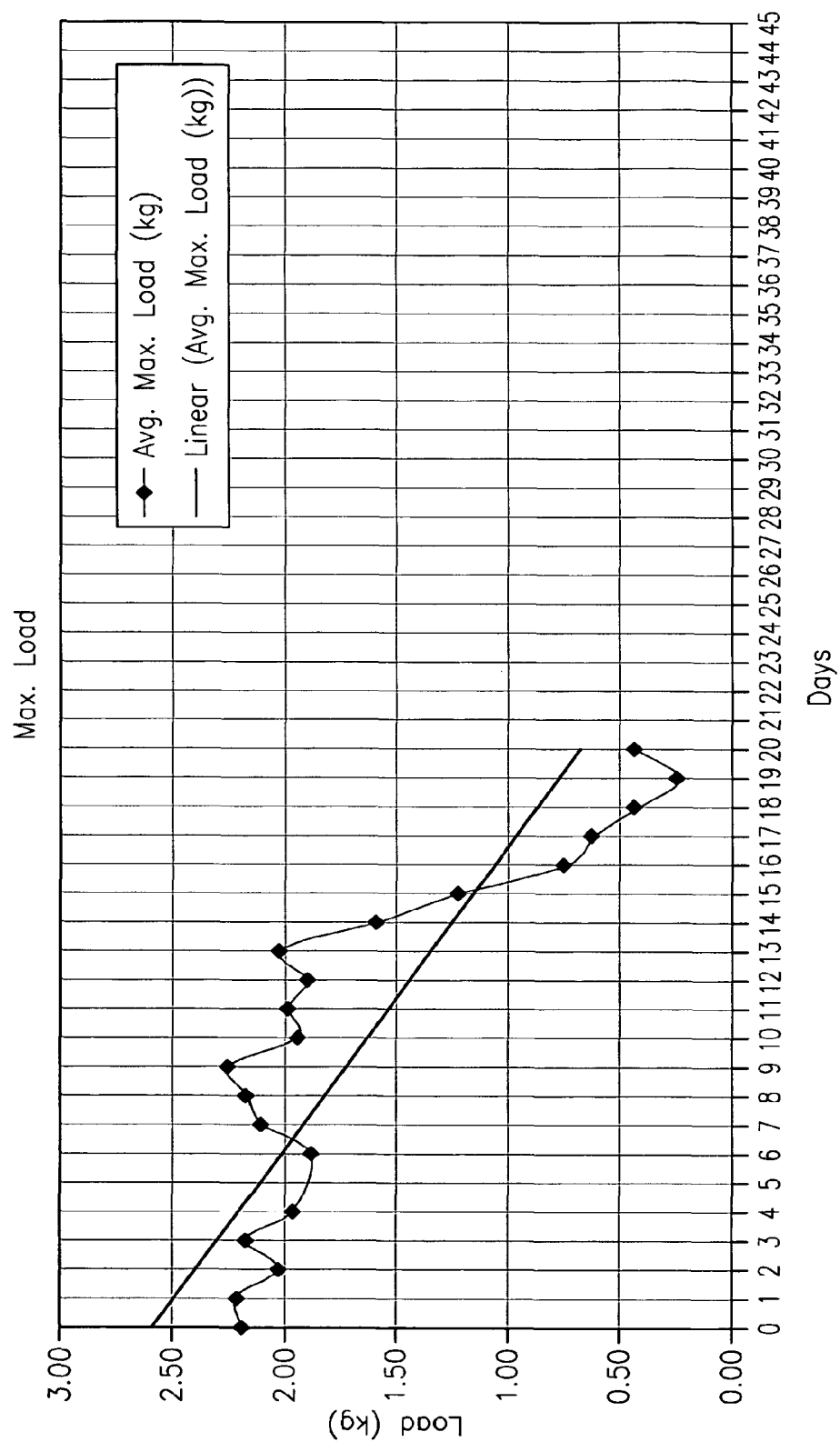
FIG. 50 is a graph depicting the reduction in the maximum load for a fastener of the present disclosure made of a glycolide-lactide copolymer treated by exposure to a low-temperature gas plasma at a pressure substantially below atmospheric.

FIG. 50 is a graph depicting the maximum load for a fastener of the present disclosure that was subjected to a low-temperature gas plasma treatment at a pressure substantially below atmospheric as disclosed in U.S. Pat. No. 5,236,563. The fasteners were made of a homopolymer of glycolic acid (100% polyglycolide). FIG. 50 depicts the results of shear force testing that was conducted after the plasma treated fasteners were placed in a saline bath simulating an in vivo environment. As can be seen in FIG. 50, at day zero the strength was 2.25 kgf (4.961 lbs), while at day fourteen the strength was 1.59 kgf (3.5 lbs). At day 15, the strength dropped to 1.21 kgf (2.67 lbs) and continued to drop in the subsequent days.

Figure 42:
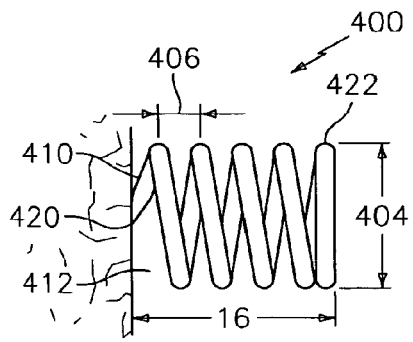
FIG. 42 depicts a perspective view of a resorbable fastener of the present disclosure, illustrating a side view of a helical fastener.
Figure 42A:
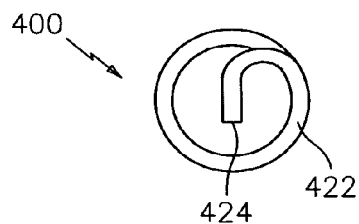
FIG. 42A depicts another perspective view of a resorbable fastener of the present disclosure, illustrating an end view of the helical fastener.

In some embodiments, the fasteners of the present disclosure may have a helical configuration. Such helical fasteners are disclosed in U.S. Pat. No. 6,562,051, the contents of which are incorporated by reference herein. These helical fasteners are depicted in FIG. 42 (including FIGS. 42A-F), FIG. 43 (including FIGS. 43A-C), FIG. 44 (including FIGS. 44A-C), and FIG. 45. Reference can be made to U.S. Pat. No. 6,562,051 for a more detailed explanation of helical fasteners depicted in FIGS. 42-45 and their use, including apparatus and/or appliers for their insertion into tissue.

Another embodiment of the present disclosure (FIGS. 42 and 42A) is embodied in a resorbable helical fastener 400 which is attached to tissue by employing an applier which rotates the fastener 400 into tissue. The dimensions and physical characteristics of the helical fastener 400 are selected to insure a secure attachment of the fastener 400 to tissue.

In a typical embodiment, the fastener 400 is formed into the configuration of a continuous helix and may have a depth 402, a diameter 404 and a pitch 406 determined by the application. The continuous helix may be longitudinally collapsible and expandable. The cross-sectional profile of the continuous helix is substantially circular in this embodiment but can be square, rectangular or triangular. In a particular application such as mesh anchoring for hernia repair, the pre-formed pitch can be 0.050 inches. However, the pre-formed pitch can vary from 0 to a maximum of approximately 3.0 times the coil diameter. In other embodiments, it is contemplated that the pitch 406 can vary along the length of the fastener 10 so as to optimize the retaining force of the fastener 400. Moreover, since the continuous helical coil is typically longitudinally collapsible and expandable, upon insertion into tissue, the final pitch 408 may be less than or greater than the pre-formed pitch. If the coil is made of rigid construction, as is also contemplated, pitch would be made substantially fixed. The diameter in this embodiment may be 5 mm; however, designs ranging from 1 mm and up are contemplated. In practice, the depth 402 of the fastener 400 must be selected so that the extent of fastener penetration into tissue is sufficient to hold the fastener 400 in place.

Figure 42B:
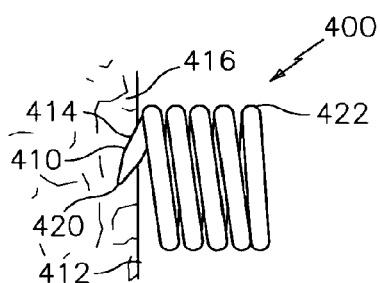
FIG. 42B depicts a schematic view of a resorbable fastener of the present disclosure, illustrating a substantially collapsed helical fastener with a relatively small gap that has been partially inserted into tissue.
Figure 42C:
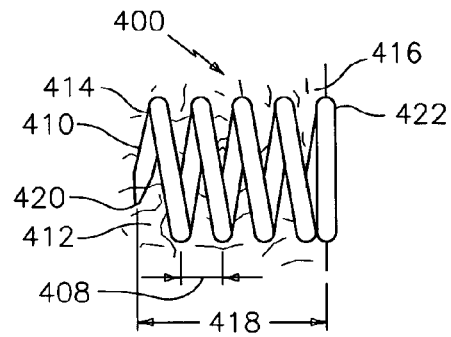
FIG. 42C depicts a schematic view of a resorbable fastener of the present disclosure, illustrating the helical fastener depicted in FIG. 42B completely inserted into tissue.
Figure 42E:
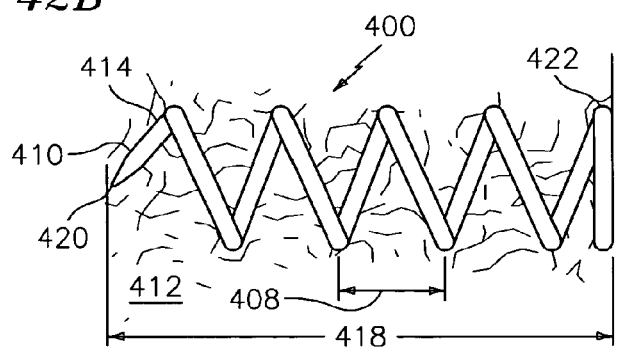
FIG. 42E depicts a schematic view of a resorbable fastener of the present disclosure, illustrating the helical fastener depicted in FIG. 42D completely inserted into tissue.
Figure 42D:
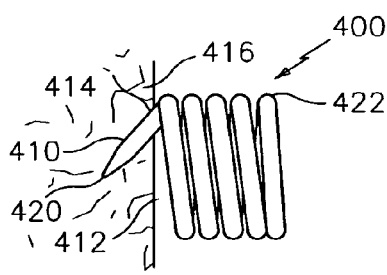
FIG. 42D depicts a schematic view of a resorbable fastener of the present disclosure, illustrating a substantially collapsed helical fastener with a relatively large gap that has been partially inserted into the tissue.
Figure 42F:
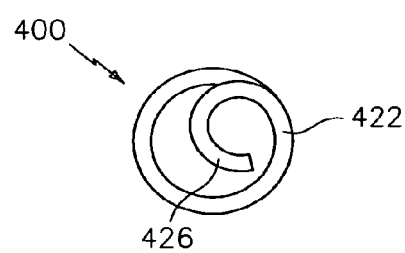
FIG. 42F depicts a perspective view of another embodiment of a resorbable fastener of the present disclosure, illustrating an end view of the helical fastener.

Moreover, distal end 410 of the fastener 400 is to be configured such that a gap 412 exists between the most distal coil 414 (or first coil) of the fastener 400 and its adjacent coil. As may be appreciated from the embodiment of FIGS. 42B through 42E, as the fastener 400 is pressed against tissue 416, all of the coils substantially collapse except the most distal coil 414, leaving the gap 412 to determine the path the fastener 400 takes as it is rotated into the tissue 416 and more importantly, the extent of penetration 418 into the tissue 416 and final pitch 408 of the fastener 400 in tissue. Although FIG. 42B shows substantially all of the coils being collapsed, it is to be appreciated that, depending upon the applicator utilized to implant the fastener 400, fewer coils than all of the coils may be collapsed at any one time. It remains, however, that since the fastener 400 is longitudinally collapsible and expandable, it is the gap 412 that generally determines final pitch 408. Accordingly, the magnitude of the gap 412 can be varied, depending upon the application, to achieve the desired final pitch 408 and penetration 418 in tissue. Thus, the greater the gap 412, upon insertion of the fastener 400 in tissue, the greater the penetration 418 and final pitch 408 of the fastener 400 in tissue.

In the typical embodiment, the distal end 410 of the helical fastener 400 terminates with a point 420. The point 420 may be sharp or blunt depending upon the tissue to which the fastener 400 will be affixed. Additionally, one or more barbs or a sharp point projecting in reverse direction to point 420 can be added (not shown) to fastener 400 near point 420 to enhance anchoring characteristics of the fastener. A proximal end 422 of the helical fastener 400 may comprise structure functioning to receive and transmit applied longitudinal forces. In this embodiment, the most proximal coil is formed into a T-bar 424 that perpendicularly sections the diameter 404 of the fastener 400. In alternate embodiments, it is also contemplated that the most proximal coil section the diameter 404 non-perpendicularly or be formed into a spiral 426 existing in a single plane (See FIG. 42F).

Figure 43:
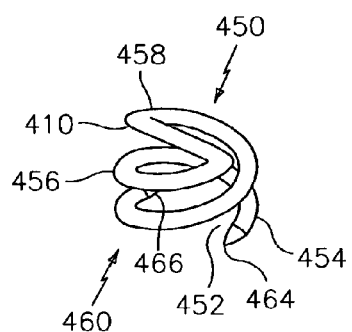
FIG. 43 depicts a perspective view of another embodiment of a resorbable fastener of the present disclosure, illustrating a double helical fastener.
Figure 43A:
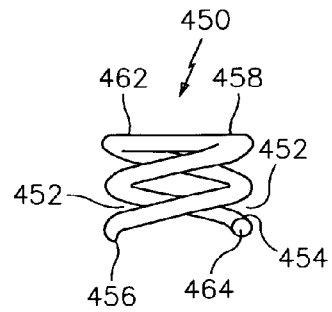
FIG. 43A is a front view of the double helical fastener of FIG. 43.
Figure 43B:
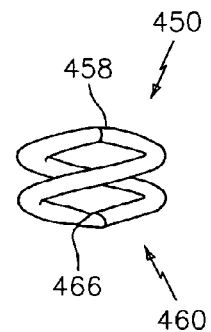
FIG. 43B is side view of the double helical fastener of FIG. 43.
Figure 43C:
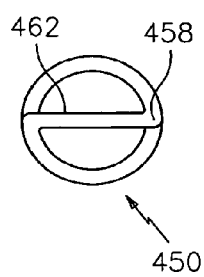
FIG. 43C is a top view of the double helical fastener of FIG. 43.

In another embodiment of the surgical fastener, the fastener 450 is formed into the configuration of a double helix (See FIGS. 43-43C). By embodying a double helix, the fastener 450 has increased retentive strength as well as means to balance the fastener 450 as it is pressed into tissue. As with the helical fastener 400, the configuration of the double helical fastener 450, i.e., the pre-formed pitch and diameter, may be varied for a particular application and a barb may be employed to enhance anchoring in tissue. Moreover, the materials contemplated are the same as those for the helical fasteners. Further, the double helical fastener 450 is also longitudinally collapsible and expandable and its final pitch is dependent upon the gap 452 existing between the most distal coils 454, 456 of the fastener 450 and their adjacent coils.

Regarding the proximal 458 and distal 460 ends of the double helical fastener 450, they comprise structure to drive the fastener into tissue as well as tissue piercing structures. The proximal end 458 has a connector bar 462 sectioning the diameter of the fastener that connects one helical coil to another and functions to receive and transmit longitudinal forces. The distal end 460 terminates with two points 464, 466 for piercing and facilitating-the implantation of the fastener 450 into tissue.

Figure 44:
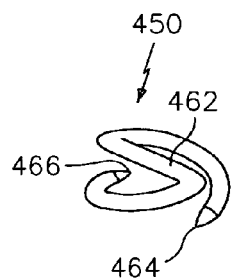
FIG. 44 is a perspective view of yet another embodiment of a resorbable fastener of the present disclosure, illustrating another design of a double helical fastener.
Figure 44A:
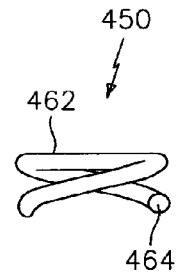
FIG. 44A is a front view of the double helical fastener of FIG. 44.
Figure 44B:
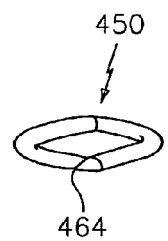
FIG. 44B is a side view of the double helical fastener of FIG. 44.
Figure 44C:
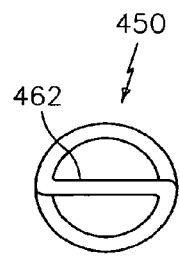
FIG. 44C is a top view of the double helical fastener of FIG. 44.

As may be appreciated by comparing FIGS. 43-43C with FIGS. 44-44C, it is contemplated that the double helical fastener 450 have a full turn design (FIGS. 43-43C) as well as a half turn design (FIGS. 44-44C). It is to be understood, however, that the designs having more than one turn and having other increments of turns are contemplated. It is the applicator that will determine the required number of turns for a specific fastener 450.

Figure 45:
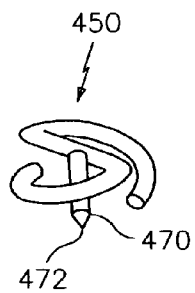
FIG. 45 is a perspective view of another resorbable fastener of the present disclosure, illustrating a helical fastener with a central post.

In yet another embodiment of the surgical fastener, as shown in FIG. 45, the double helical fastener 450 is provided with a pivot post 470 having a pointed terminal end 472. The pivot post 470 of this embodiment operates to provide the fastener 450 with a stabilizing element so that, as the fastener 450 is being turned, the helical coils cooperatively enter the tissue.

Figure 46:
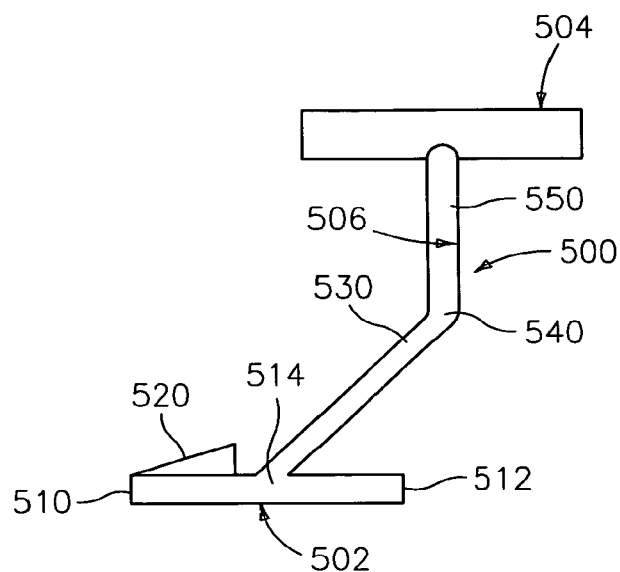
FIG. 46 shows a plan view of a resorbable fastener having a clip configuration according to the present disclosure.
Figure 47:
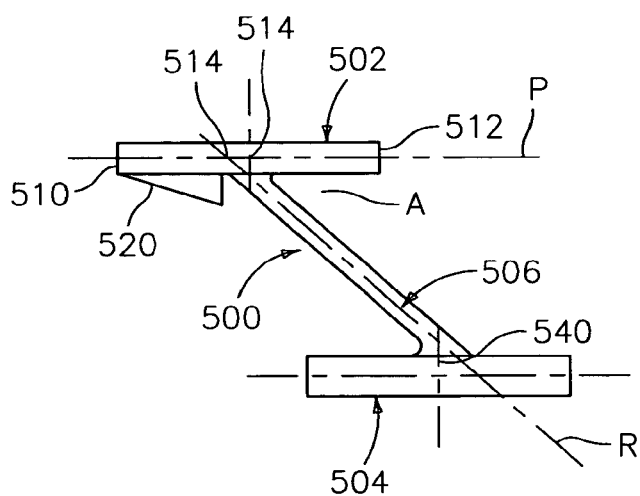
FIGS. 47 and 48 show another embodiment of a resorbable fastener having a clip configuration according to the present disclosure.
Figure 48:
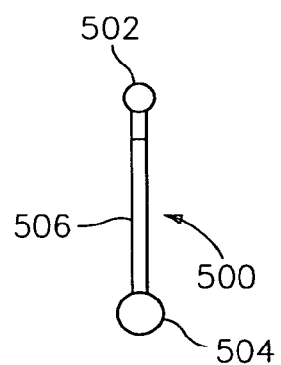

In another embodiment, the fasteners of the present disclosure may have a clip structure, such as the clip depicted in FIGS. 46-48. FIG. 46 shows a first embodiment of a clip fastener according to the present disclosure. Clip 500 has a monolithic structure including a distal anchoring rod 502 and a proximal stop bar 504 which are linked via connecting rod 506. Distal anchoring rod 502 and proximal stop bar 504 extend transversely with respect to connecting rod 506. Anchoring rod 502 and proximal stop bar 504 extend on either side of connecting rod 506 in such a way as to form an "H".

Anchoring rod 502 extends in a first direction P of penetration and spacing-apart of an anatomical support 508, in which direction said rod is introduced. The connecting rod 506 extends in a second direction R of retention in which clip 500 is retained in the flesh, by traction from the proximal stop bar 504. Connecting rod 506 is arranged relative to anchoring rod 502 so as to have an inoperative position in which the connecting rod 506 is arranged along the direction of retention R, and a stressed position of penetration, folded back against the anchoring rod 502, in which the connecting rod 506 is arranged parallel to the direction of penetration P. When connecting rod 506 is folded back against the anchoring rod 502, the clip is then introduced through the prosthetic part (not shown) and into the flesh, via the distal end 510 of the anchoring rod 502, by a push on the proximal end 512 of this same rod 502. When anchoring rod 502 has completely penetrated into the support, for example a muscle wall, the angulation at the junction 514 between the anchoring rod 502 and the connecting rod 506 acts, at the first traction on the clip, in such a way as to bring the connecting rod 506 back perpendicular to the anchoring rod 502, in its inoperative position. The clip thus is retained between two planes of muscle fibers. At the same time, the proximal stop bar 504 arrests the penetrative displacement of the anchoring rod 502, by coming into abutment against the prosthetic part (not shown).

The anchoring rod 502 in the first place includes a spacing projection 520 acting as a harpoon or barb extending away from the distal end 510 in the direction toward the proximal end 512. This spacing projection 520 has a surface inclined toward the proximal part of the clip. The inclination of a surface of the projection 520 makes it possible to ensure the spacing apart of the anatomical support, and also to displace the bending stress, exerted by the prosthetic tissue and the muscle wall on connecting rod 506, further in the direction of the proximal stop bar 504, that is to say higher up on the connecting rod 506, as is represented in FIG. 46. The elevation of the bending stress point, caused by the projection, allows the connecting rod 506 to align itself in a substantially parallel manner to the direction of penetration P, without excessively stressing the junction between the anchoring rod 502 and the connecting rod 506.

Still referring to FIG. 46, the connecting rod 506 is inclined in a part 530 relative to the direction of penetration P of the anchoring rod 502, for example at 45°. Moreover, the connecting rod 506 has a bend 540 and extends in another part 550 from the latter toward the stop bar 504, by forming a substantially right angle therewith, in such a way that the stop bar 504 remains substantially parallel to the anchoring rod 502.

In accordance with FIGS. 47 and 48, and according to a second embodiment of the invention, the clip 500 has, as before, a monolithic structure, and comprises a distal anchoring rod 502 in the anatomical support, a proximal stop bar 504 relative to the prosthetic part, and a connecting rod 506 made in one piece linking the distal anchoring rod 502 and the proximal stop bar 504. As before, the connecting rod 506 is arranged relative to the distal anchoring rod 502 so as to determine at least two positions of this connecting rod 506, namely: an inoperative position in which the connecting rod 506 is arranged along a first direction R; and a stressed position in which the connecting rod 506 is folded back along a second direction P, corresponding to the direction of penetration into the anatomical support of the distal anchoring rod 502, and this against the latter.

According to the present disclosure, in the inoperative position of the connecting rod 506, the first direction R is inclined relative to the second direction P, parallel or identical to that of the anchoring rod 502, and this at an angle for example equal to about 45°.

The connecting rod 506 joins the distal anchoring rod 502 at an intermediate point 514 of the latter, for example at the center.

As has been described with reference to FIG. 46, the distal anchoring rod 502 includes at least one spacing projection 520, having the form of a barb or harpoon, provided in the direction P, extending away from the distal end 510 in the direction toward the proximal end 512 of the distal anchoring rod 502.

The connecting rod 506 joins the proximal stop bar 504 at an intermediate point 540 of the latter, for example at the center.

The proximal bar 504 has a larger cross section than that of the distal anchoring rod 502. The connecting rod 506 has an intermediate cross section between those of the proximal stop bar 504 and of the distal anchoring element 502, respectively.

In the inoperative position of the connecting rod 506, corresponding to the configuration of the clip before its use, this connecting rod, the proximal stop bar 504 and the distal anchoring rod 502 are arranged substantially in the same plane. The stop bar 504 and the anchoring rod 502 are arranged substantially parallel to one another, with the connecting rod 506 in an inclined or oblique position relative to the stop bar 504 and to the anchoring rod 502.

Methods for repairing tissue with the fasteners of the present disclosure are also provided. As noted above, the surgical fasteners of the present disclosure may be utilized in a hernial repair method, wherein a surgical mesh is secured in place over a hernia repair site by imbedding the surgical fasteners in to body tissue through the surgical mesh. In addition, fasteners of the present disclosure may be utilized to attach one tissue to another including, but not limited to, attaching tissue to a ligament.

Desirably, resorbable screw fastener 10 may be delivered within an endoscopic 5 mm-diameter shaft of a fastener applier capable of firing multiple fasteners. Components of an applier that may be used in the firing of resorbable screw fasteners is shown and described in U.S. Pat. No. 5,830,221, the entire disclosure of which is incorporated herein by reference.

Figure 5:
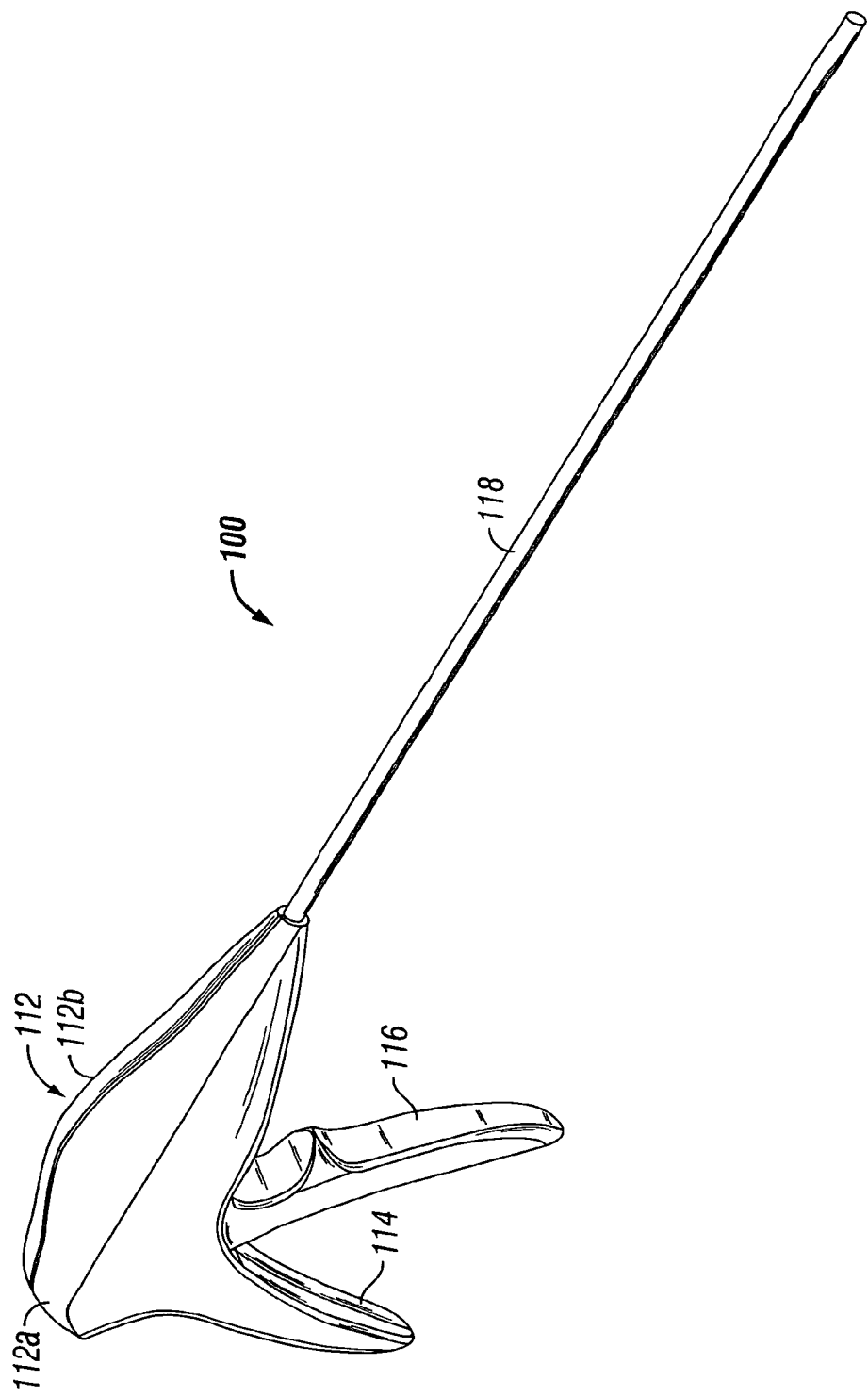
FIG. 5 is a perspective view of an embodiment of a screw fastener applier according to an embodiment of the present disclosure.
Figure 6:
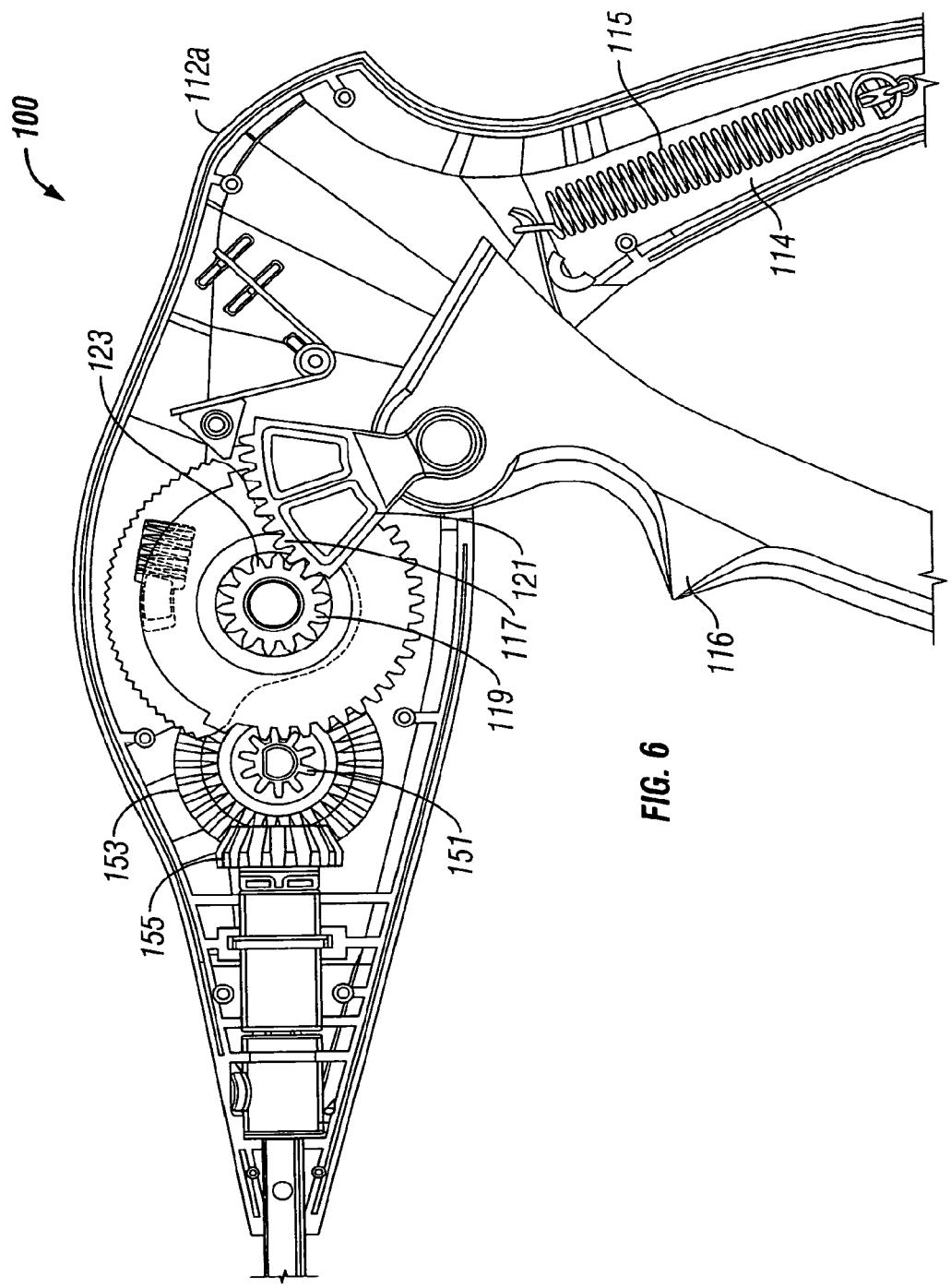
FIG. 6 is a side view, with a housing half removed, of the housing portion of the screw fastener applier of FIG. 5 while in an initial position.

Referring now to FIGS. 5 and 6, a fastener applier for applying resorbable screw fasteners 10 is shown generally as fastener applier 100. Fastener applier 100 generally includes a proximal housing portion 112, which may be formed as two separate housing halves 112a and 112b and a handle portion 114 extending from housing 112. A trigger 116 is movably mounted to housing 112. Trigger 116 may be pivotally connected to housing 112 with a free end of trigger 116 spaced from a free end of handle portion 114. This arrangement provides an ergonomic advantage and positive secure control of trigger 116 and fastener applier 100. Fastener applier 100 also includes an elongated tubular portion 118 extending distally from housing 112. The elongated tubular portion 118 is provided to retain a plurality of screw fasteners 10 for application to body tissue. Elongated tubular portion 118 is dimensioned to fit through conventional endoscopic tubes or cannula structures inserted through small incisions in the body. In general, manipulation of control trigger 116 results in ejection of screw fasteners 10, one by one, out of elongated tubular portion 118 and into body tissue.

Figure 8:
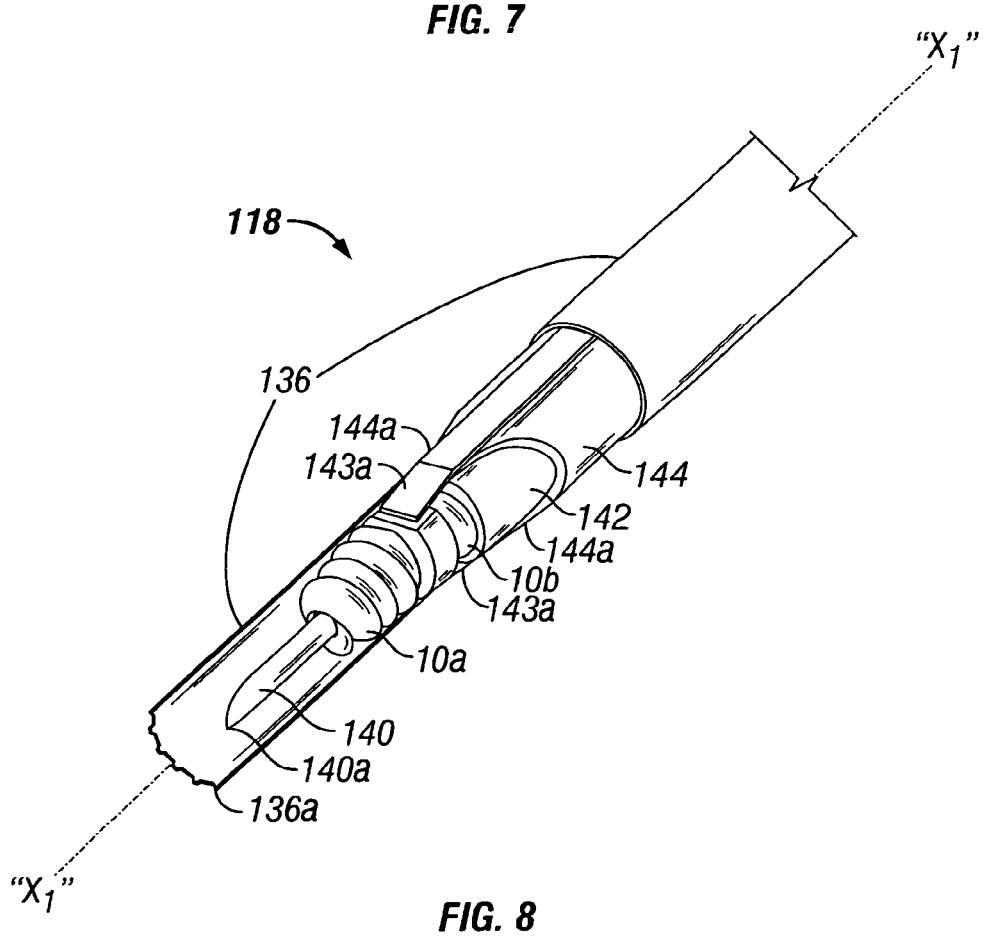
FIG. 8 is a perspective partial cross-sectional cut-away view of the distal end of the screw fastener applier of FIGS. 5 and 6.

With continued reference to FIG. 6, operation of housing portion 112 of fastener applier 100 is described. In an initial or starting position, trigger 116 is biased away from handle 114 due to the force of return spring 115. As shown, teeth 117 of gear portion 121 of trigger 116 are engaged with teeth 119 of trigger gear 123. As trigger 116 is squeezed, teeth 117 engage teeth 119 of trigger gear 123 to rotate driver gear 151, which, in turn, rotates a first bevel gear 153 which, in turn, rotates a bevel drive gear 155 and ultimately cylindrical driver 144, fastener retainer 142 and pilot 140 (as seen in FIG. 8). Reference may be made to U.S. Pat. No. 5,830,221, previously incorporated herein by reference, for a detailed discussion of the operation of housing portion 112 of fastener applier 100.

Figure 7:
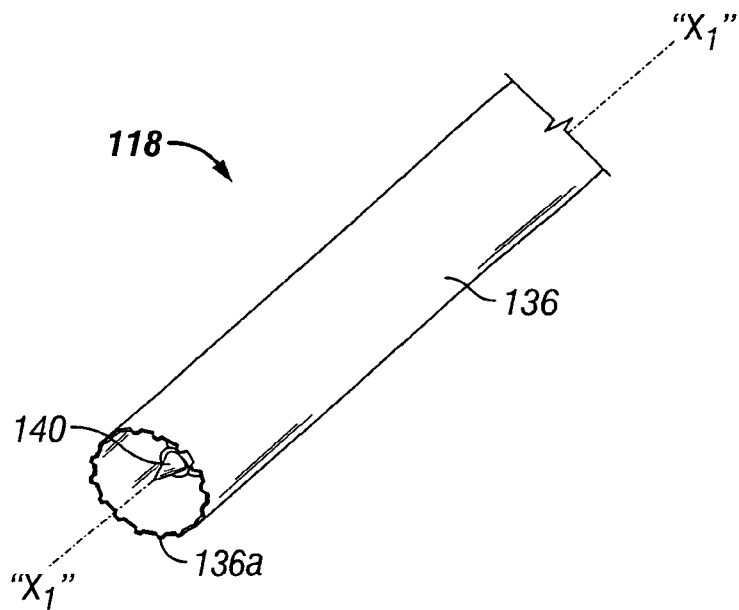
FIG. 7 is a perspective view of a distal end of the screw fastener applier of FIG. 5.

Referring to FIGS. 7-8, elongated tubular portion 118 includes an outer tube 136, defining a longitudinal axis "X1" and housing a cylindrical driver 144. Cylindrical driver 144 generally includes a longitudinally extending pilot 140, and a cylindrical fastener retainer 142 extending along the length of cylindrical driver 144. Fastener retainer 142 is configured to receive a plurality of screw fasteners 10 and pilot 140 therein, such that upon rotation of cylindrical driver 144, screw fasteners 10 and pilot 140 are similarly rotated. A plurality of screw fasteners 10 may be arranged in a series longitudinally along the length of a distal portion of cylindrical driver 144. Each screw fastener 10 is positionable within fastener retainer 142 of cylindrical driver 144.

Cylindrical driver 144 includes a pair of opposed resilient fingers or tabs 144a extending from a distal-most end thereof. Each resilient finger 144a includes a distal tip 143a angled and/or otherwise oriented toward the longitudinal "X1" axis. As seen in FIG. 8, resilient fingers 144a of cylindrical driver 144 hold or pinch a distal-most screw fastener 10a in position ready for application. In particular, distal tip 143a of each resilient finger 144a of cylindrical driver 144 is seatable in or receivable in respective slots 28 formed in head portion 14 of screw fastener 10 (see for instance FIG. 1). In operation, cylindrical driver 144 functions to engage a plurality of fasteners and to facilitate turning and driving/advancing of screw fasteners 10 into tissue.

Outer tube 136 may additionally be provided with a crenellated distal tip 136a for engaging mesh overlying the surgical site in order to maintain the mesh firmly in position and prevent the mesh from thrusting or otherwise spinning or bunching while resorbable screw fastener 10 is torqued and driven through the mesh. Crenellated distal tip 136a, of outer tube 136, may be of various geometric shapes and dimensions, (e.g., serrated, saw-toothed, etc.), or may be omitted completely.

Figure 9:
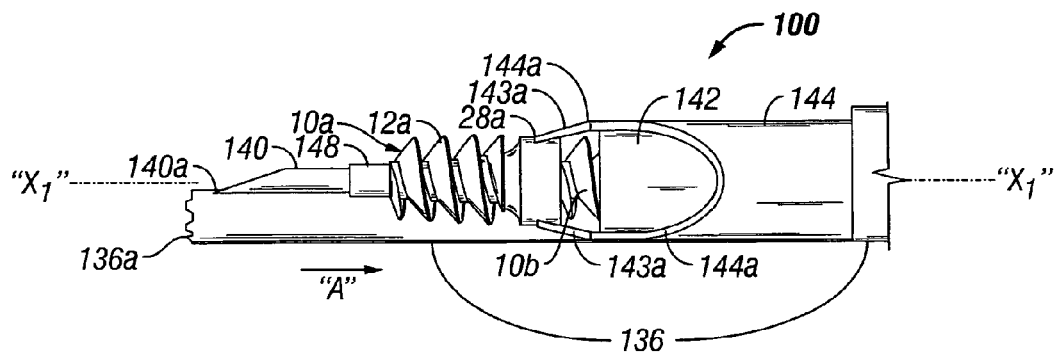
FIGS. 9-17 are partial cross-sectional or cut-away side elevational views of the distal end of the screw fastener applier of FIGS. 5-8, illustrating a series of operational steps of the screw fastener applier for driving the resorbable screw fastener of FIGS. 1-4 into the target surgical site.
Figure 10:
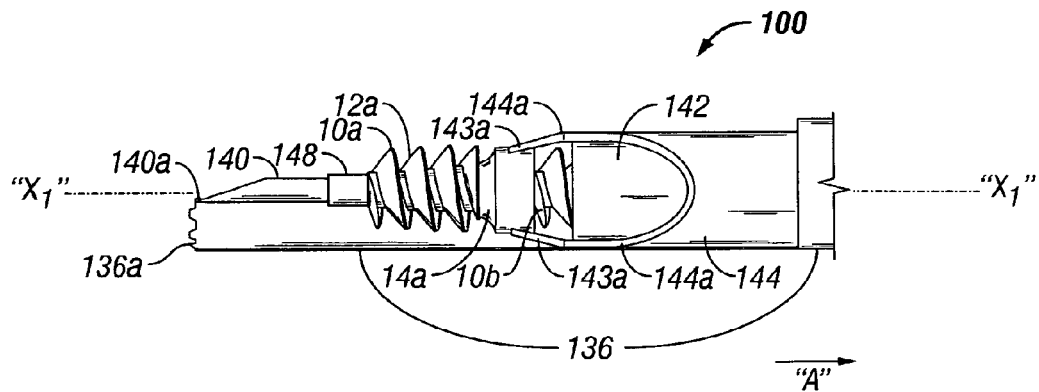

Pilot 140 functions as a guide to aid in the insertion of screw fastener 10 into tissue. Pilot 140 includes a sharpened distal tip 140a for tapping the mesh and underlying target tissue prior to insertion of screw fastener 10. Distal tip 140a of pilot 140 is shown with an angled tip. In an alternative embodiment, distal tip 140a of pilot 140 may be of various geometries. Referring to FIGS. 9-10, retaining feature 148, provided on pilot 140, holds a distal-most screw fastener 10a in place as will be described below. In a loaded position, fastener applier 100 includes at least one screw fastener 10 disposed in or retained in fastener retainer 142 such that pilot 140 extends through cannulated opening 18 of screw fastener 10. As explained above, slots 28 of head portion 14 of screw fastener 10 are engaged by respective tips 143a of fingers 144a of cylindrical driver 144. Tips 143a of fingers 144a of cylindrical driver 144 are configured and dimensioned to engage and/or be received in respective slots 28 formed in head portion 14 of screw fastener 10.

A method of inserting resorbable screw fastener 10, using fastener applier 100, will now be discussed. Referring to FIGS. 5, 6 and 9-17, distal tip 136a of outer tube 136 is initially placed against the mesh and/or the target tissue. Advantageously, crenellated tip 136a of outer tube 136 securely engages the mesh and helps to prevent movement of the mesh relative to the tissue. The user then pushes distal tip 136a of outer tube 136 against the target mesh or tissue. In so doing, a spring (not shown) is compressed allowing outer tube 136 to retract proximally, in the direction of arrow "A" (see FIG. 9), and thus unlocking a trigger lock (not shown).

As a safety feature, as seen in FIG. 10, pilot 140 remains within outer tube 136 even when outer tube 136 is fully retracted. This safety feature prevents accidental contact or pricking with distal tip 140a of pilot 140.

Figure 11:
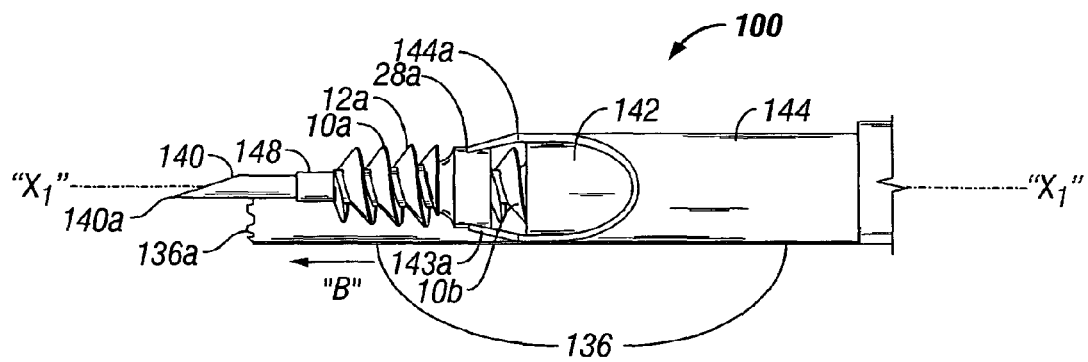
Figure 17:
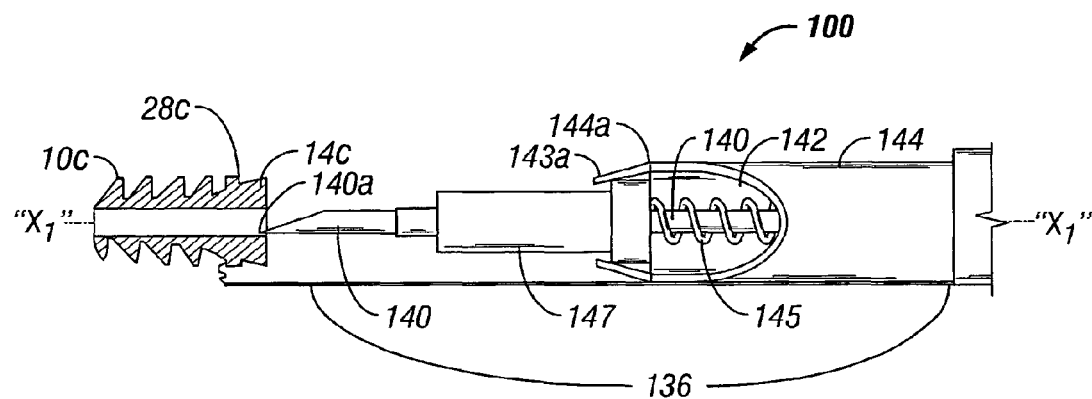

Referring now to FIGS. 6, 11 and 17, with outer tube 136 in the fully retracted position, fastener applier 100 is capable of firing screw fastener 10 therefrom. To drive and/or expel fastener(s) 10 from fastener applier 100, trigger 116 is drawn toward handle 114 against the bias of return spring 115. As trigger 116 is moved, teeth 117 on gear portions 121 of trigger 116 engage and rotate teeth 119 of trigger gear 123 clockwise, ultimately causing cylindrical driver 144, fastener retainer 142 and pilot 140 to be driven (axially in the direction of arrow "B") and rotated (about the longitudinal "X1" axis) until pilot 140 extends beyond distal tip 136a of outer tube 136 of fastener applier 100, as shown in FIG. 11. In one embodiment, pilot 140 extends beyond distal tip 136a of outer tube 136 by an amount approximately equal to 3 mm. Feed spring 145 acts on a plunger 147 to bias plunger 147 against the proximal-most screw fastener and maintain a force in the distal direction on the column of screw fasteners 10 disposed within fastener retainer 142.

Figure 12:
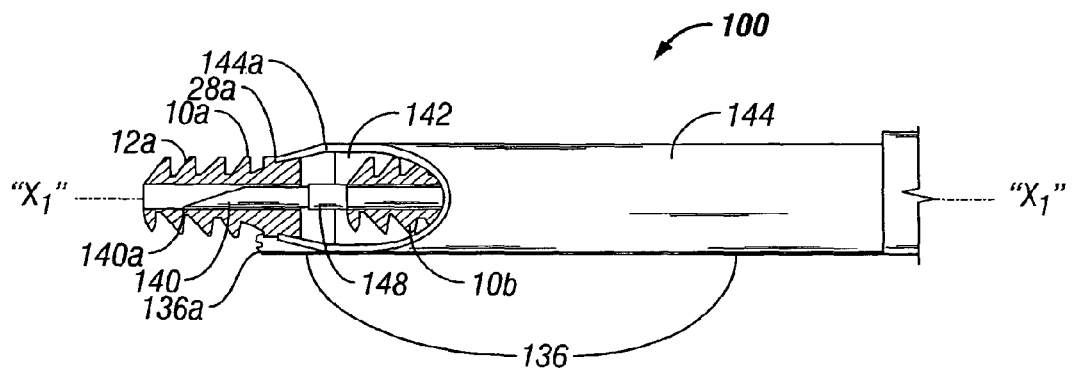

As shown in FIG. 12 and as will be discussed in greater detail below, once pilot 140 has stopped moving distally, cylindrical driver 144 and fastener retainer 142 continue to be driven and rotated distally until head portion 14 of a distal-most resorbable screw fastener 10a is substantially in line with distal tip 136a of outer tube 136 thus preventing insertion of distal-most screw fastener 10a beyond distal tip 136a of outer tube 136. As shown in FIG. 12, cylindrical driver 144 drives and rotates distal-most screw fastener 10a completely over and beyond retaining feature 148 of pilot 140. Additionally, retaining feature 148 acts as a stop to the distal advancement of an adjacent resorbable screw fastener 10b, adjacent distal-most screw fastener 10a, until adjacent screw fastener 10b is engaged and advanced by cylindrical driver 144.

Retaining feature 148 may be in the form of a C-ring, compressible O-ring, a crimp or bump in the cannulated lumen 18 (see FIG. 15A) or the like, wherein retaining feature 148 has an initial dimension which is greater than the dimension of cannulated lumen 18 of screw fastener 10. Accordingly, when distal-most screw fastener 10a initially engages or contacts retaining feature 148, since retaining feature 148 is sized to be larger than cannulated lumen 18, distal-most screw fastener 10a is prevented from passing. However, as the force being applied to distal-most screw fastener 10a is increased, retaining feature 148 is caused to be squeezed into cannulated lumen 18 as distal-most fastener 10a is advanced. Distal-most fastener 10a is forced entirely across retaining feature 148 such that the retaining feature passes through cannulated lumen 18 and exits a proximal end thereof. The column of screw fasteners, behind distal-most fastener 10a is then distally advanced by the force of feed spring 145. However, the force of feed spring 145 is not great enough to cause retaining feature 148 to be squeezed into the next screw fastener. Accordingly, retaining feature 148 prevents the distal advancement of the column of screw fasteners.

Figure 13:
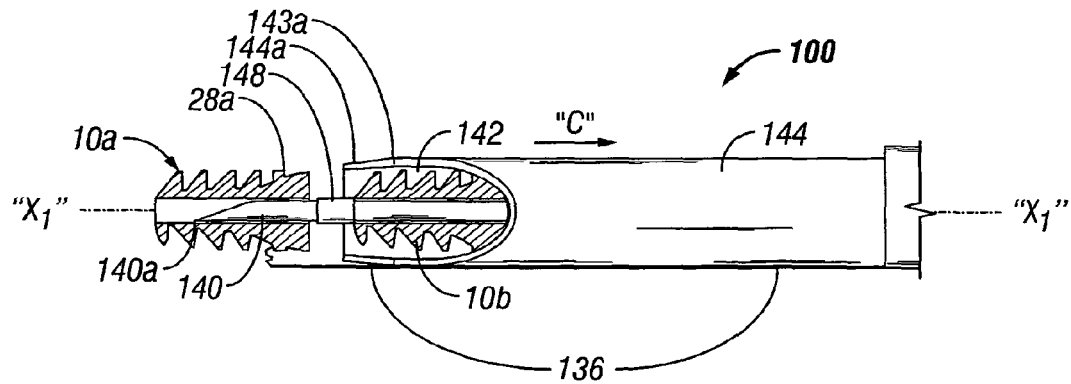

Once trigger 116 has been completely depressed and distal-most screw fastener 10a is driven through the mesh and into the tissue, the user releases trigger 116 and a two stage release cycle begins. Referring to FIG. 13, while fastener retainer 142 remains fixed in place, cylindrical driver 144 is retracted in a proximal direction (e.g., in the direction of arrow "C"). Cylindrical driver 144 is not rotated and drawn in a proximal direction so that distal-most fastener 10a is not unscrewed. As cylindrical driver 144 is retracted resilient fingers 144a deflect or cam radially outward as resilient fingers 144a slide over the tapered surface of slots 28a to disengage slots 28a of head portion 14a of distal-most screw fastener 10a and release distal-most screw fastener 10a. In addition, as cylindrical driver 144 is retracted resilient fingers 144a are cammed radially outward by their inter-engagement with fastener retainer 142. Cylindrical driver 144 may be retracted until a distal-most tip of resilient fingers 144a is substantially aligned with a distal-most edge of fastener retainer 142.

Figure 14:
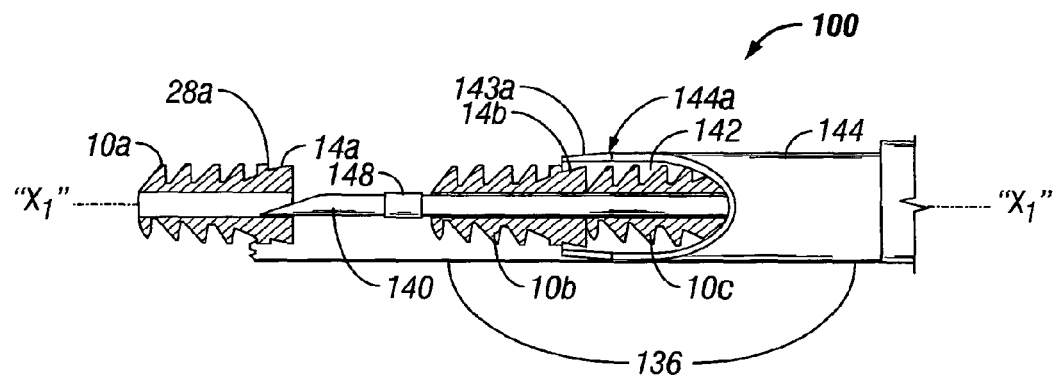

Referring now to FIG. 14, pilot 140 is proximally retracted until pilot 140 is disposed within outer tube 136 such that distal tip 140a of pilot 140 is not longer exposed. Additionally, cylindrical driver 144 and fastener retainer 142 are proximally retracted until tips 143a of resilient fingers 144a of cylindrical driver 144 are aligned with slots 28b formed in head portion 14b of adjacent screw fastener 10b. In an alternative embodiment, cylindrical driver 144 and pilot 140 may retract independently of one another or simultaneously.

Figure 15:
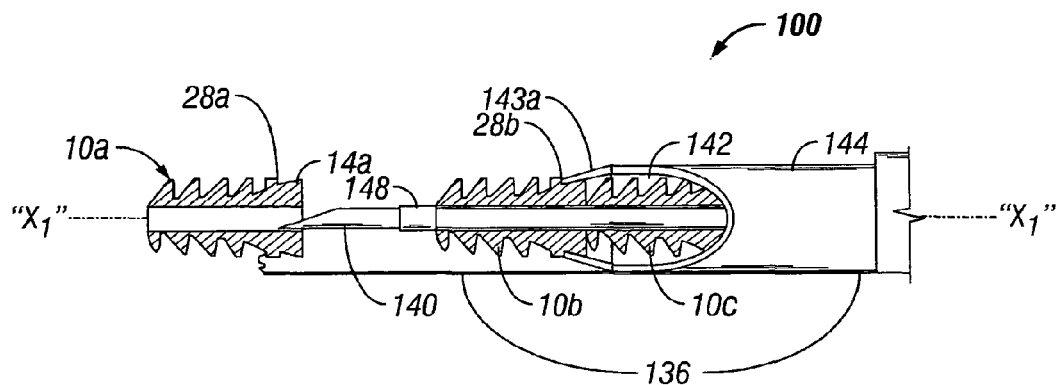
Figure 15A:
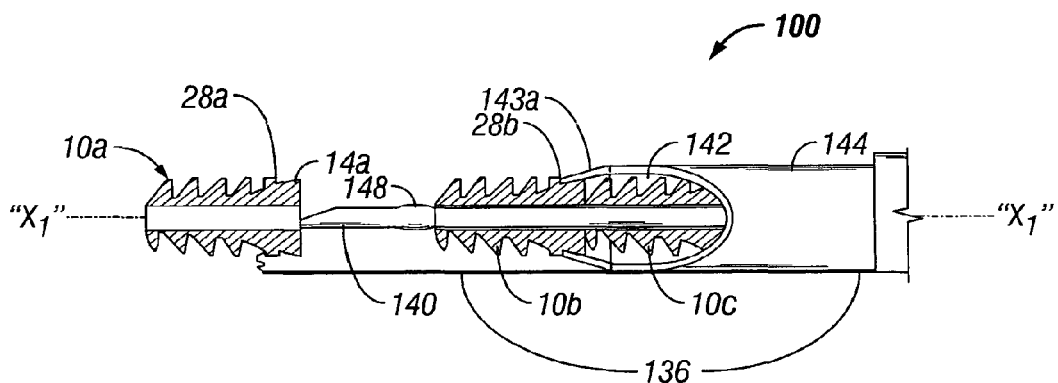
Figure 16:
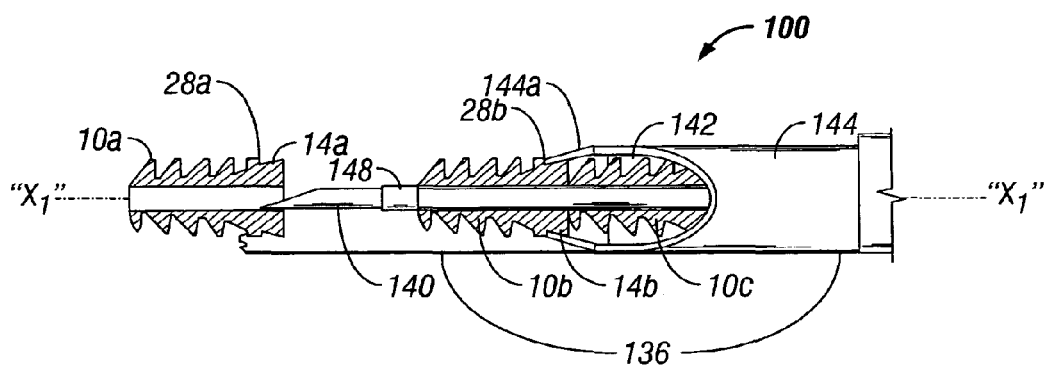

Referring now to FIG. 15, while screw fastener 10b is maintained in position by retaining feature 148, fastener retainer 142 is proximally retracted, to its starting position, as shown in FIG. 8, so that tips 143a of resilient fingers 144a of cylindrical driver 144 return to their un-deflected position and engage slots 28b of head portion 14b of adjacent screw fastener 10b. Since fastener retainer 142 has a longer stroke to return to its starting position as compared to cylindrical driver 144 resilient fingers 144a of cylindrical driver 144 flex back down and engage adjacent screw fastener 10b. Referring to FIG. 16, outer tube 136 is returned to its starting position, as shown in FIGS. 9 and 17. In alternative embodiments, distal movement of outer tube 136 to its starting position can be accompanied by an audible and/or tactile response heard/felt by the end user. In alternative embodiments cylindrical driver 144 and fastener retainer 142 can proximally retract together.

In an embodiment, housing 112 may be fabricated to have a reusable handle portion 114 and trigger 116 that can be re-sterilized, and a disposable elongated tubular portion 118. Thus, upon discharge of all the screw fasteners 10 elongated tubular portion 118 would be discarded and replaced, housing portion 112 would be sterilized and reused up to a limited number of procedures.

In other embodiments, revolving means to cause cylindrical driver 144 to rotate may include a single knob connected to a rotator which can be turned by hand. Additionally, the revolving means may include a rack and gear structure or a set of beveled gears.

Figure 18:
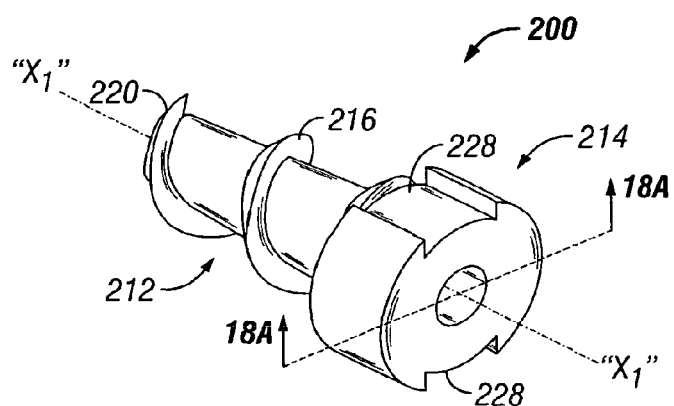
FIG. 18 is a perspective view of another embodiment of a resorbable screw fastener of the present disclosure.
Figure 18A:
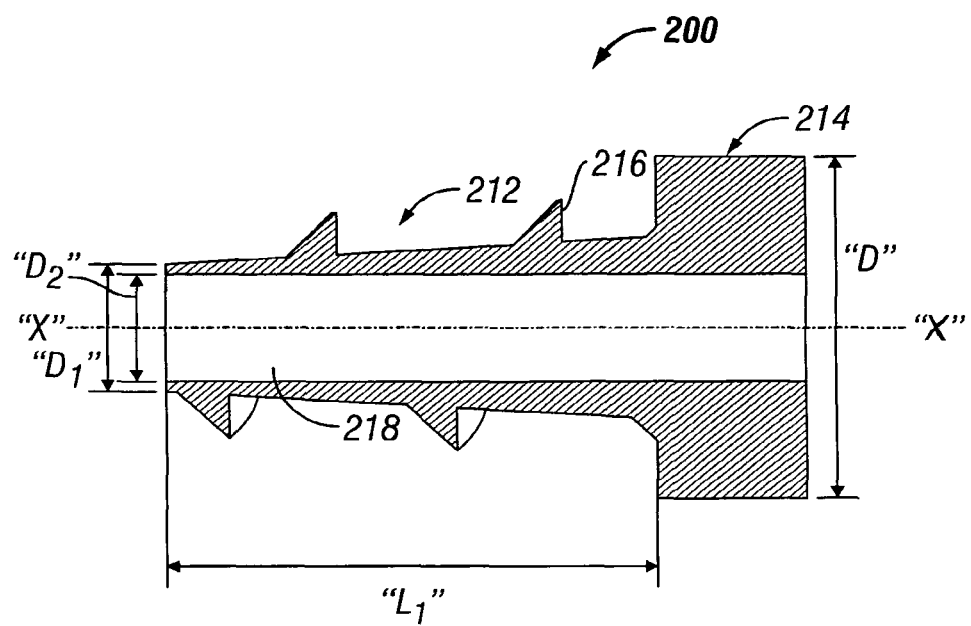
FIG. 18A is a longitudinal cross-sectional view of the resorbable screw fastener of FIG. 18 taken along line 18A-18A of FIG. 18.
Figure 18B:
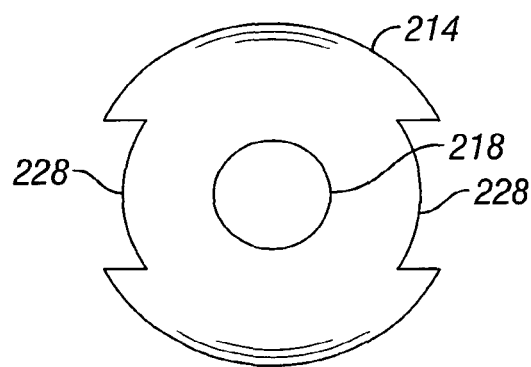
FIG. 18B is a top view of the resorbable screw fastener of FIGS. 18 and 18A.

FIGS. 18, 18A and 18B present another possible embodiment of the resorbable screw fastener. Screw fastener 200 is similar to screw fastener 10 and will only be discussed in detail to the extent necessary to identify differences in construction and/or operation. In one embodiment, body portion 212 of screw fastener 200 has a uniform distance along at least a portion of, desirably along its entire, length which is equal to inner distance "D2". Also, distance "D1" of body portion 212 may be tapered from a narrow, blunt distal end 220 to a larger proximal end where it transitions into the outside diameter of proximal head portion 214 to increase torque strength. The gradual taper along body portion 212 allows a small footprint of screw fastener 200 when entering the mesh, and growing radially outward along the length of body portion 212 for better rates of resorption into the body and then transitions into the outside diameter of head portion 214 to help resist torque. In addition, slots 228, formed in head portion 214 are parallel to the longitudinal axis "X" axis and extend the entire thickness of head portion 214.

Discussion of other fastener appliers which may be utilized with fasteners herein, especially screw fasteners, include those disclosed in International Application PCT/US04/18702, (especially FIGS. 19-36 thereof), the contents of which are incorporated by reference herein.

Figure 19:
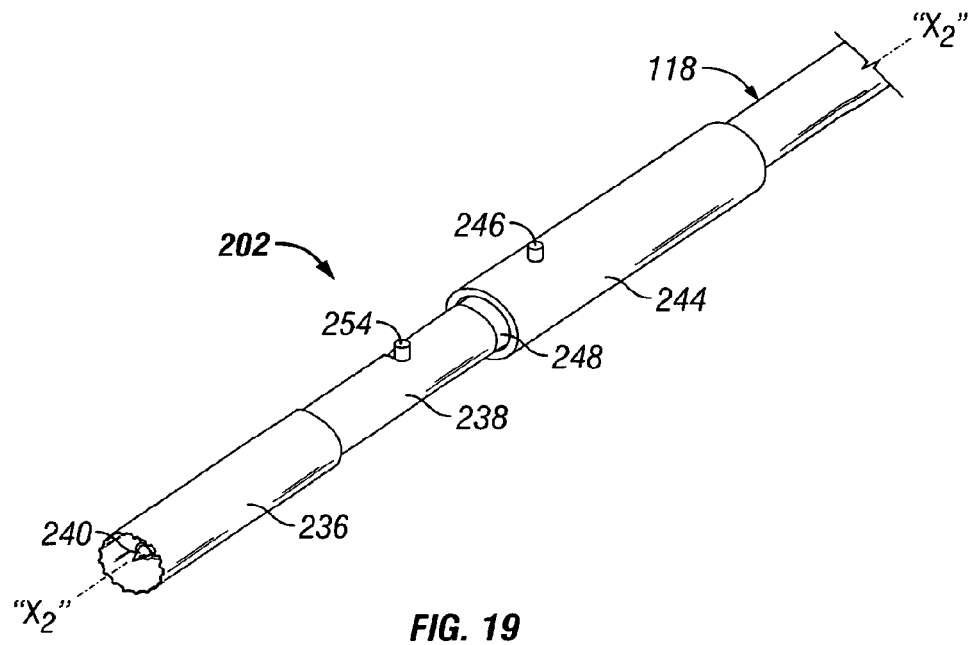
FIG. 19 is a perspective view of a distal end of a screw fastener applier according to another embodiment of the present disclosure, with an end effector operatively secured thereto.
Figure 20:
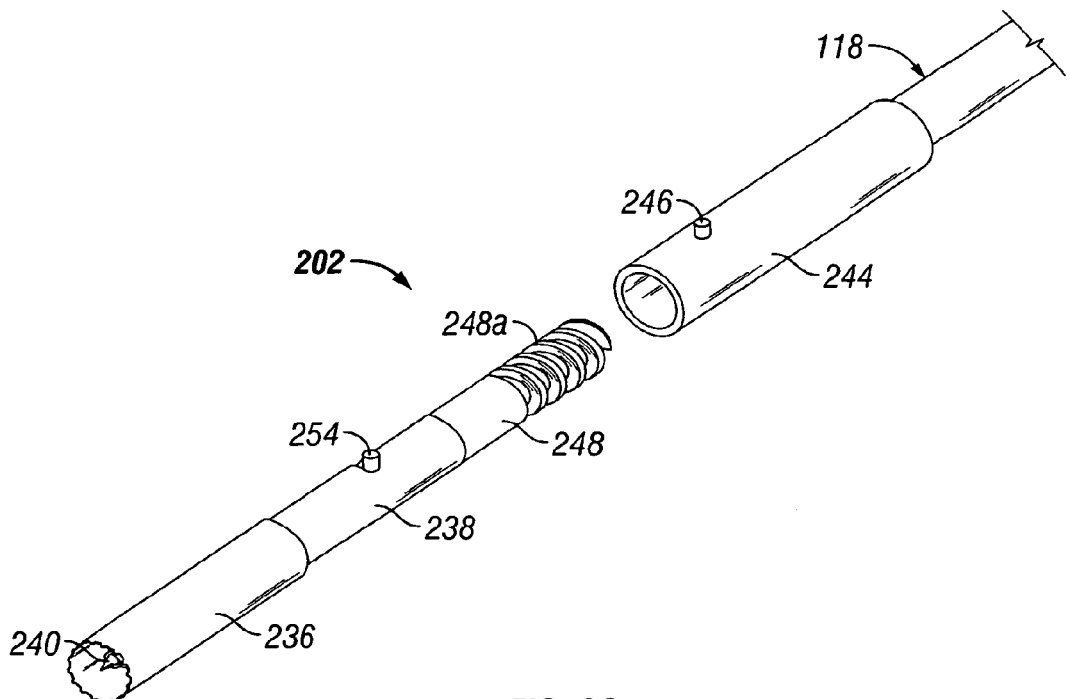
FIG. 20 is a perspective view of the distal end of the screw fastener applier of FIG. 19, with the end effector separated or disconnected therefrom.
Figure 21:
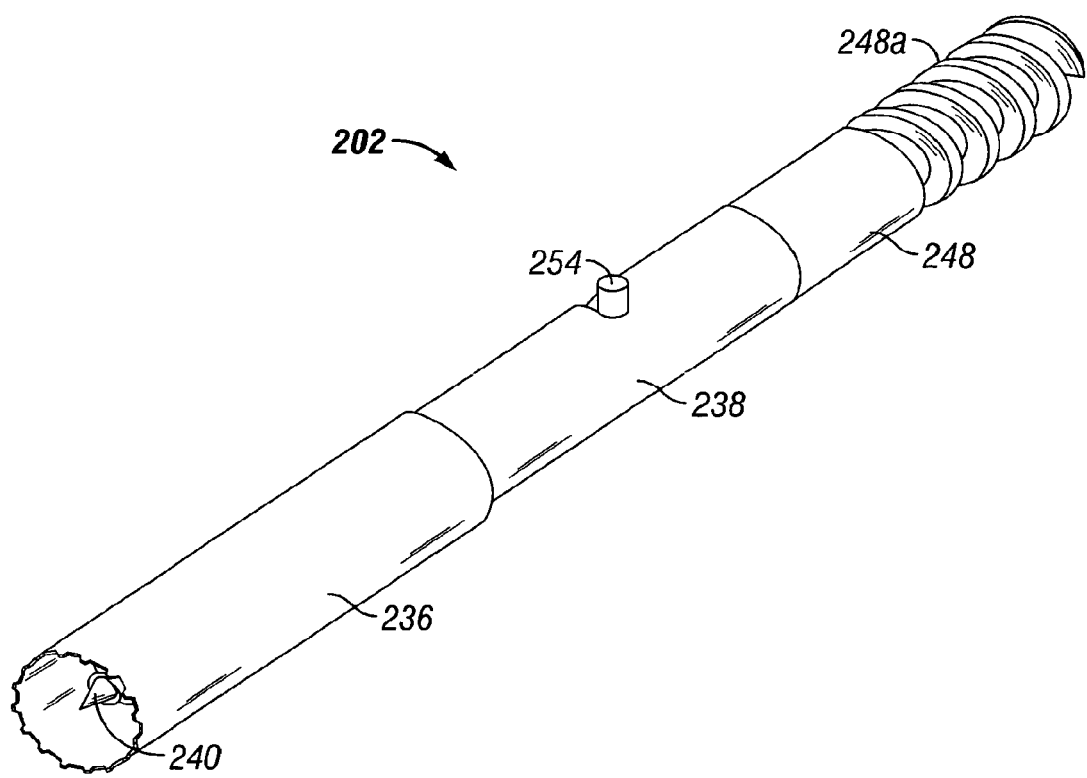
FIG. 21 is a perspective view of the assembled cam spiral sub-assembly, inner tube sub-assembly and outer tube of the end effector according to the present disclosure.

With reference to FIGS. 19-21, an end effector for engagement with a distal end of elongated tubular portion 118 of fastener applier 100, to be used for the application of screw fasteners 10 or 200 or for retaining screw fasteners 10 or 200, is generally designated as 202. End effector 202 may take the form of a disposable loading unit (DLU) or single use loading unit (SULU) which retains a load of fasteners 10 or 200 therein, and which may be disposed of or replaced or may be sterilized, re-loaded and reused.

Referring initially to FIGS. 19-21, end effector 202 includes an outer tube 236, defining longitudinal axis "X2" and housing an inner tube assembly 238 for retaining screw fasteners 200 therein, a cam spiral driver 244 supported on the distal end of tubular portion 118, a pin 254 and a cam spiral sub-assembly 248 disposed in inner tube assembly 238 and operatively connected to cam spiral drive 244.

End effector 202 is attached to or formed integral with the distal end of elongated tubular portion 118 of fastener applier 100 such that when control trigger 116 of fastener applier 100 is drawn toward handle 114, cam spiral driver 244 rotates (similar to the rotation of cylindrical driver 144 described above). Cam spiral sub-assembly 248 includes a helical thread 248a, which mates with and receives a pin 246 of cam spiral driver 244 so that when cam spiral driver 244 rotates, cam spiral sub-assembly 248 rotates and translates, as discussed in detail hereinbelow.

Figure 22:
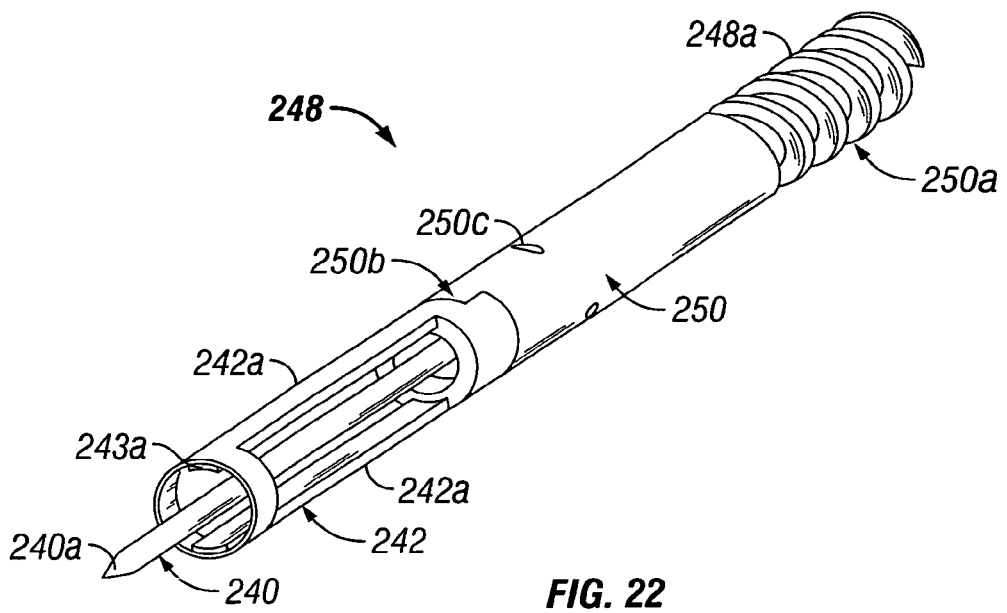
FIG. 22 is a perspective view of a cam spiral sub-assembly of the end effector of FIG. 21 with the outer tube and inner tube sub-assembly removed therefrom.
Figure 23:
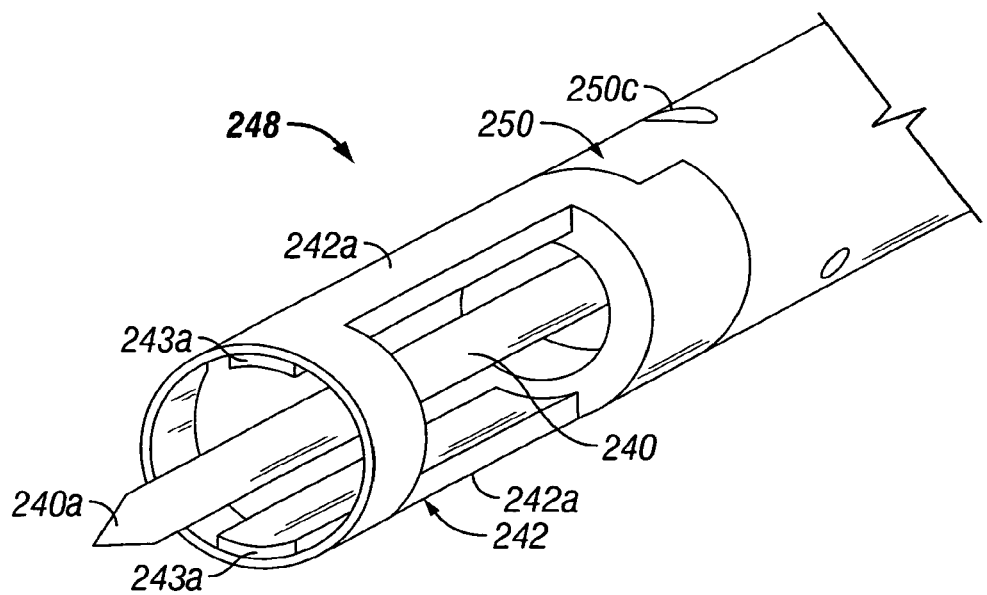
FIG. 23 is a further perspective view of the cam spiral sub-assembly of FIG. 22.
Figure 24:
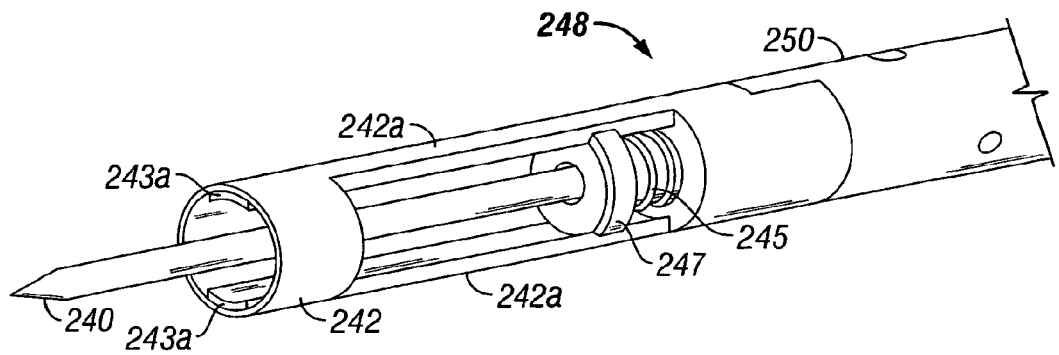
FIG. 24 is a perspective view of the cam spiral sub-assembly of FIGS. 22 and 23, with a pusher and feed spring shown operatively associated therewith.

Referring to FIGS. 22 and 23, cam spiral sub-assembly 248 will be discussed in detail. Cam spiral sub-assembly 248 includes a cam spiral 250 having a proximal end 250a defining a helical thread 248a, pilot 240 extending longitudinally from a distal end 250b of cam spiral 250, and a fastener retainer 242 operatively supported on distal end 250b of cam spiral 250. Cam spiral sub-assembly 248 is assembled in such a manner that upon rotation of cam spiral 250, pilot 240 and fastener retainer 242 are similarly rotated. In alternative embodiments, cam spiral sub-assembly 248 may be fabricated as a single part/component. Fastener retainer 242 may include a pair of opposed longitudinally extending rails 242a which act as retainers or guides for screw fasteners 200. A distal end 243a of rails 242a will also act as a driver for screw fasteners 200, as will be described hereinbelow. Desirably, a distal end 240a of pilot 240 extends distally of distal end 243a of rails 242a and fastener retainer 242. A pin 254 (see for instance FIG. 21) is received in and extends radially from a slot 250c formed in cam spiral 250.

Figure 25:
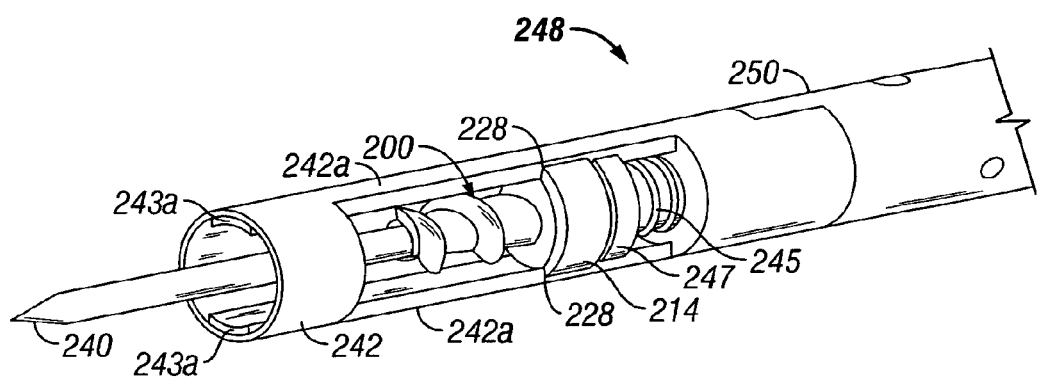
FIG. 25 is a perspective view of the cam spiral sub-assembly of FIG. 24, illustrating a screw fastener operatively associated therewith.
Figure 26:
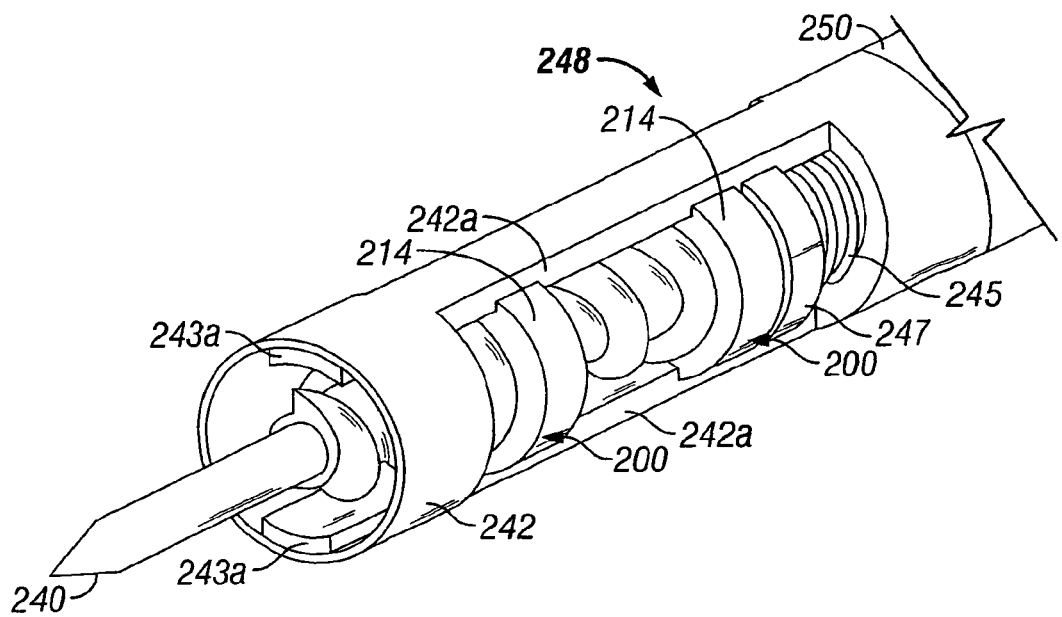
FIG. 26 is a perspective view of the cam spiral sub-assembly of FIGS. 24 and 25, with a pair of screw fasteners operatively associated therewith.
Figure 27:
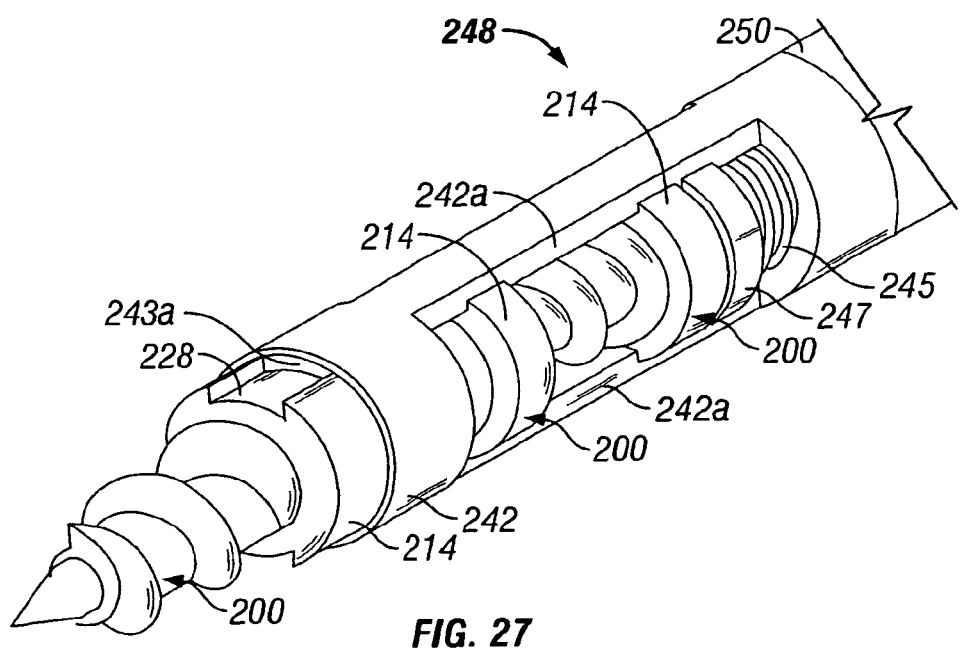
FIG. 27 is a perspective view of the cam spiral sub-assembly of FIGS. 24-26, with at least three screw fasteners operatively associated therewith.

A seen in FIGS. 24-27, cam spiral sub-assembly 248 further includes a feed spring 245 and a screw fastener pusher 247, each disposed on pilot 240 and within fastener retainer 242. As shown in FIGS. 25-27, rails 242a of fastener retainer 242 orients screw fasteners 200 by engaging respective slots 228 in head portion 214 of screw fastener 200. Desirably, feed spring 245 is disposed between screw fastener pusher 247 and cam spiral 250. As such, feed spring 245 biases pusher 247 in a distal direction.

Multiple screw fasteners 200 may be retained in or operatively associated with cam spiral sub-assembly 248, for example, one(1) as seen in FIG. 25, two (2) as seen in FIG. 26, or three (3) as seen in FIG. 27. While one to three screw fasteners 200 are shown in FIGS. 25-27, it is understood that the present device may be used with or may accommodate any number of screw fasteners 200.

Figure 28:
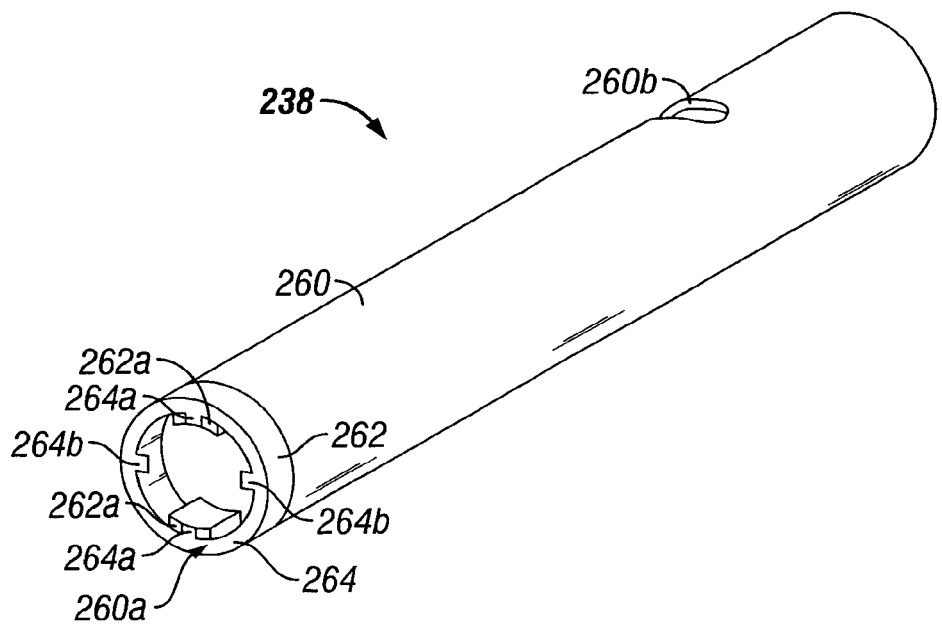
FIG. 28 is a perspective view of the inner tube sub-assembly of the end effector of FIGS. 21 and 28.

Referring now to FIG. 28, in an alternate embodiment or additionally, inner tube sub-assembly 238 includes a cylindrical body 260, a torque ring 262 operatively connected to a distal end 260a thereof, and a retaining ring 264 operatively connected to torque ring 262. Cylindrical body 260, includes a transversely oriented rotational slot 260b formed therein for slideably receiving pin 254 extending from cam spiral 250. Rotational slot 260b limits the movement of pin 254 and, in turn, the rotation of cam spiral driver 244. Rotational slot 260b may be sized to limit the rotation to about 90 degrees. With continued reference to FIG. 28, torque ring 262 includes a pair of diametrically opposed engagement features 262a extending radially inward therefrom. Engagement features 262a are desirably sized to mate with corresponding slots 228 of head portion 214 of screw fastener 200. Retaining ring 264 includes two pair of diametrically opposed tabs 264a, 264b extending radially inward therefrom. Tabs 264a, 264b may be offset by about 90 degrees relative to one another. Desirably, one pair of tabs 264a is axially aligned with engagement features 262a of torque ring 262. Tabs 264a, 264b hold distal screw fastener 200 in place and prevent feed spring 245 of cam spiral sub-assembly 248 from driving all the internal screw fasteners 200 out from the instrument in one rapid fire sequence.

Inner tube sub-assembly 238 may be constructed from several different components mounted or otherwise operatively connected to one another to form a unitary inner tube sub-assembly 238 or may be manufactured as a single component.

Figure 29:
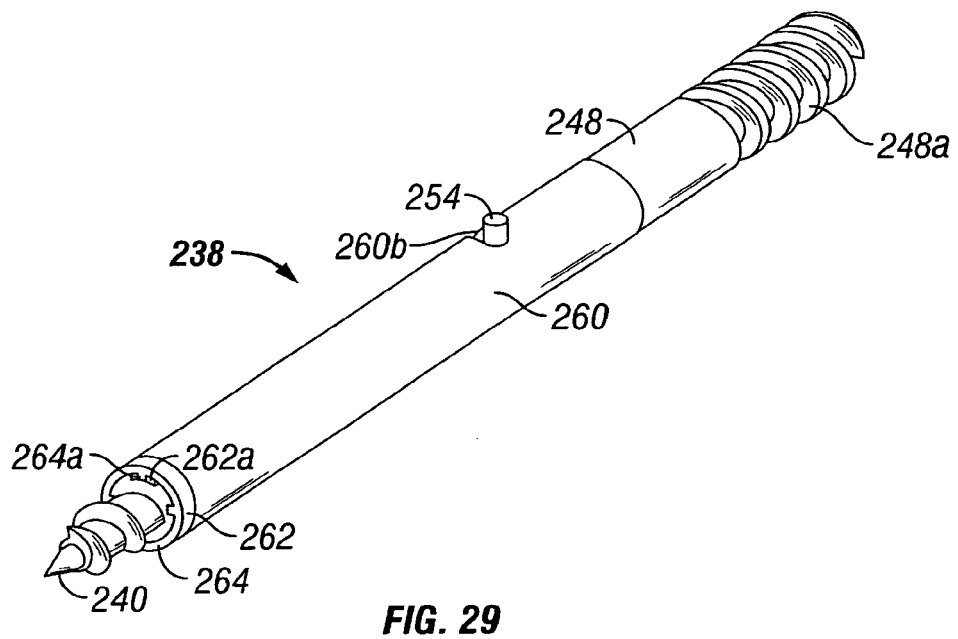
FIG. 29 is a perspective view of the cam spiral sub-assembly of FIG. 27 operatively disposed within the inner tube sub-assembly of FIG. 28, while in a first position.
Figure 30:
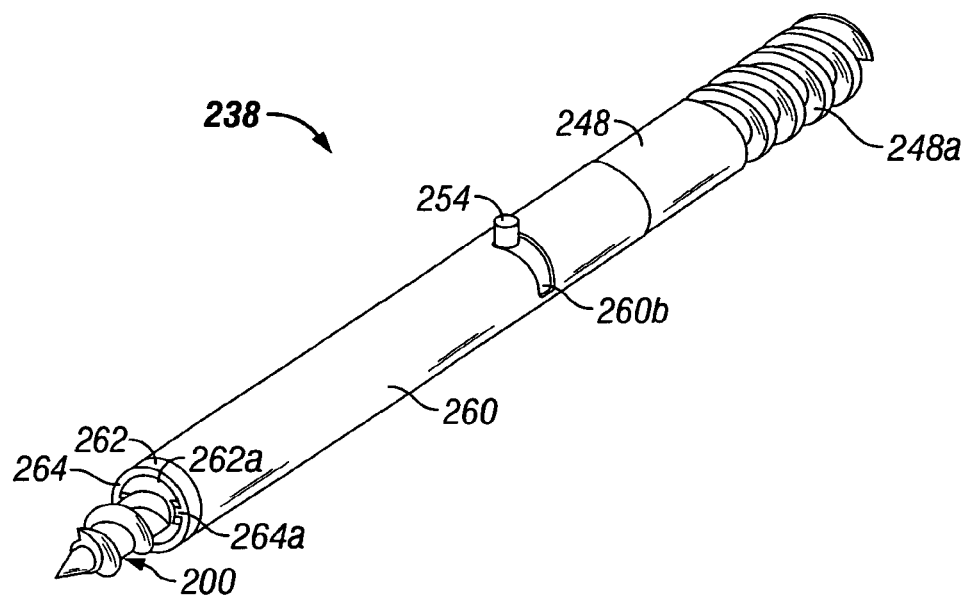
FIG. 30 is a perspective view of the cam spiral sub-assembly and inner tube sub-assembly of FIG. 29, while in a second position.
Figure 31:
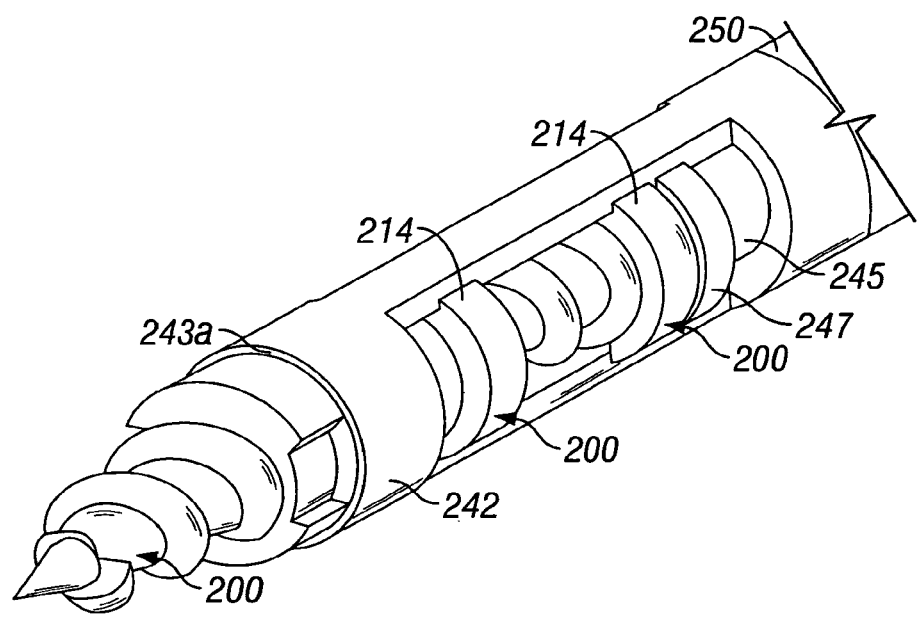
FIG. 31 is a perspective view of the cam spiral sub-assembly of FIG. 27, while in the second position of FIG. 30.

Referring now to FIGS. 29 and 30, inner tube sub-assembly 238 is shown operatively associated with (e.g., rotatably supported on) cam spiral sub-assembly 248. As described above, pin 254 extends through rotational slot 260b of inner tube sub-assembly 238. Accordingly, inner tube sub-assembly 238 and cam spiral sub-assembly 248 act as one unit when cam spiral sub-assembly 248 is activated, as will be described in greater detail below.

In FIG. 29, inner tube subassembly 238 is shown in a first position with respect to cam spiral sub-assembly 248 and with pin 254 located at one end of rotational slot 260. In FIG. 30, inner tube sub-assembly is shown in a second position with respect to cam spiral sub-assembly 248 and with pin 254 located at an opposite end of rotational slot 260.

Figure 32:
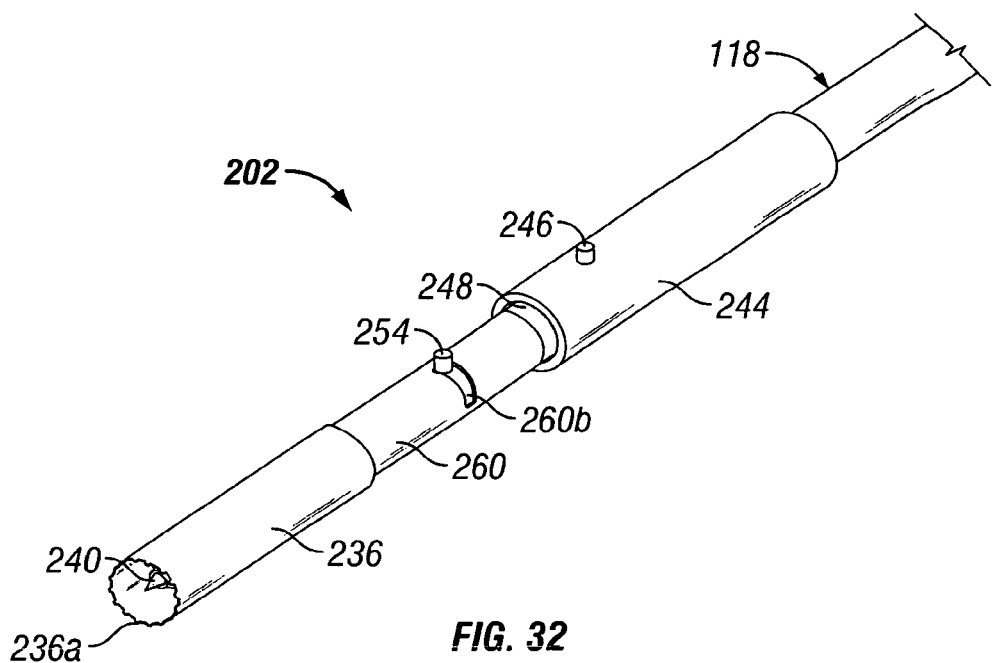
FIGS. 32-36 illustrate a series of operational steps of the surgical fastener applier including the end effector of FIGS. 19-31 for driving the resorbable screw fastener of FIGS. 18, 18A and 18B into the target surgical site.
Figure 33:
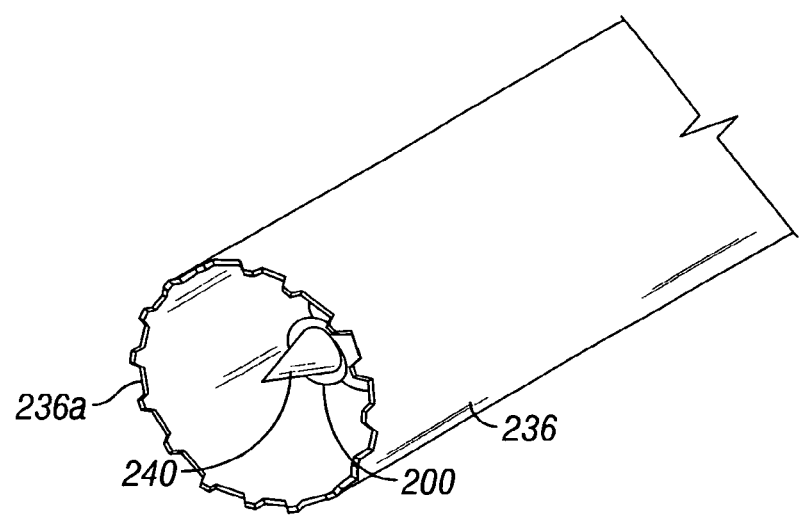

Turning now to FIGS. 31-36, a method of inserting resorbable screw fastener 200 or 10 will be discussed. Referring to FIGS. 32 and 33, a distal tip 236a (shown crenellated) of outer tube 236 is initially placed against the mesh and/or the target tissue. In so doing, distal tip 236a of outer tube 236 helps to maintain outer tube 236 firmly connected to the mesh and keeps the mesh taught.

Figure 34:
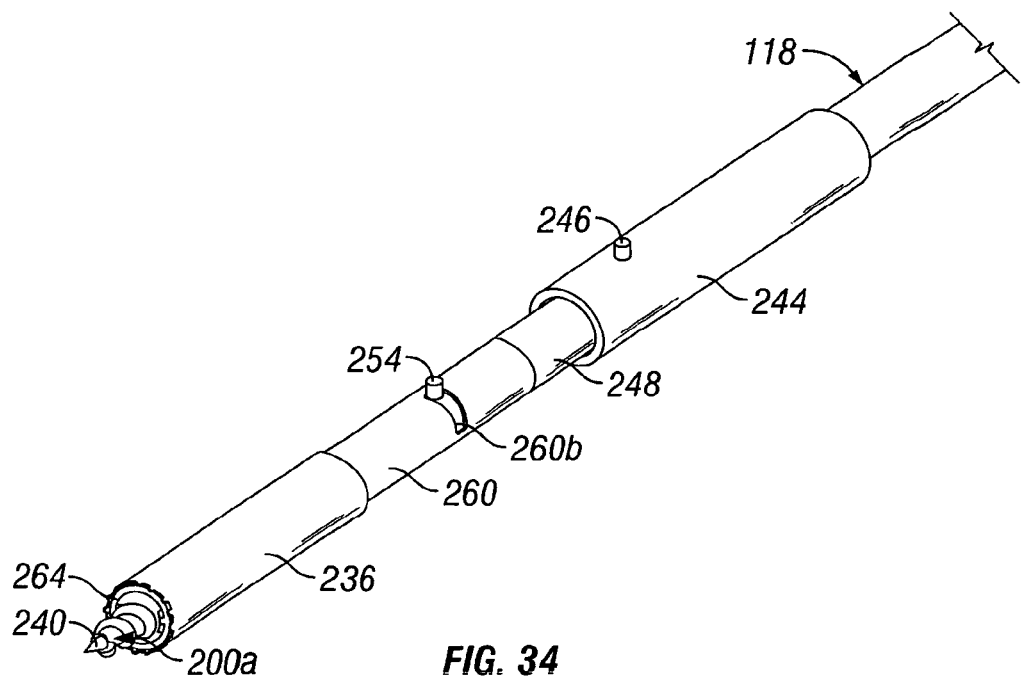
Figure 35:
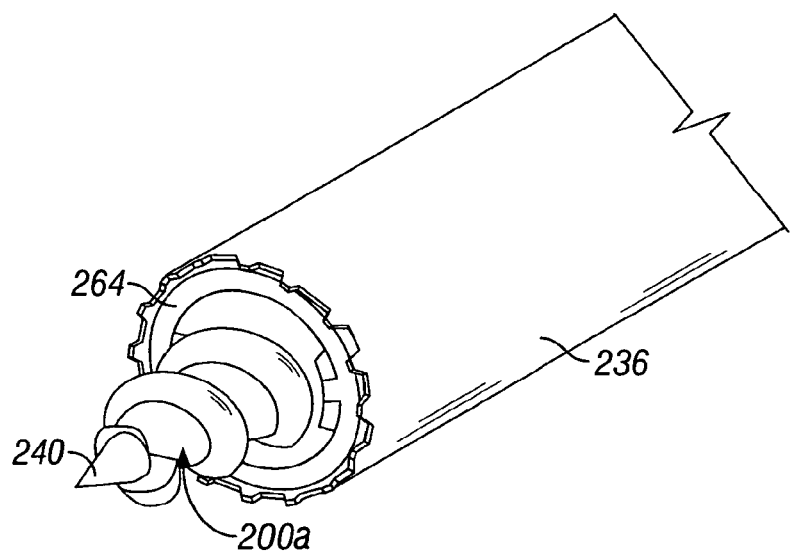

Next, the trigger of the fastener applier is actuated (e.g., squeezed) to rotate cam spiral driver 244 and to rotate and translate cam spiral sub-assembly 248 and inner tube sub-assembly 238. Holding outer tube 236 in a stationary position, a distal-most screw fastener 200a is advanced distally as shown in FIGS. 34 and 35. In particular, as cam spiral sub-assembly 248 is rotating and translating to drive distal-most screw fastener 200a forward, inner tube sub-assembly 238 rotates distal-most screw fastener 200a.

Figure 36:
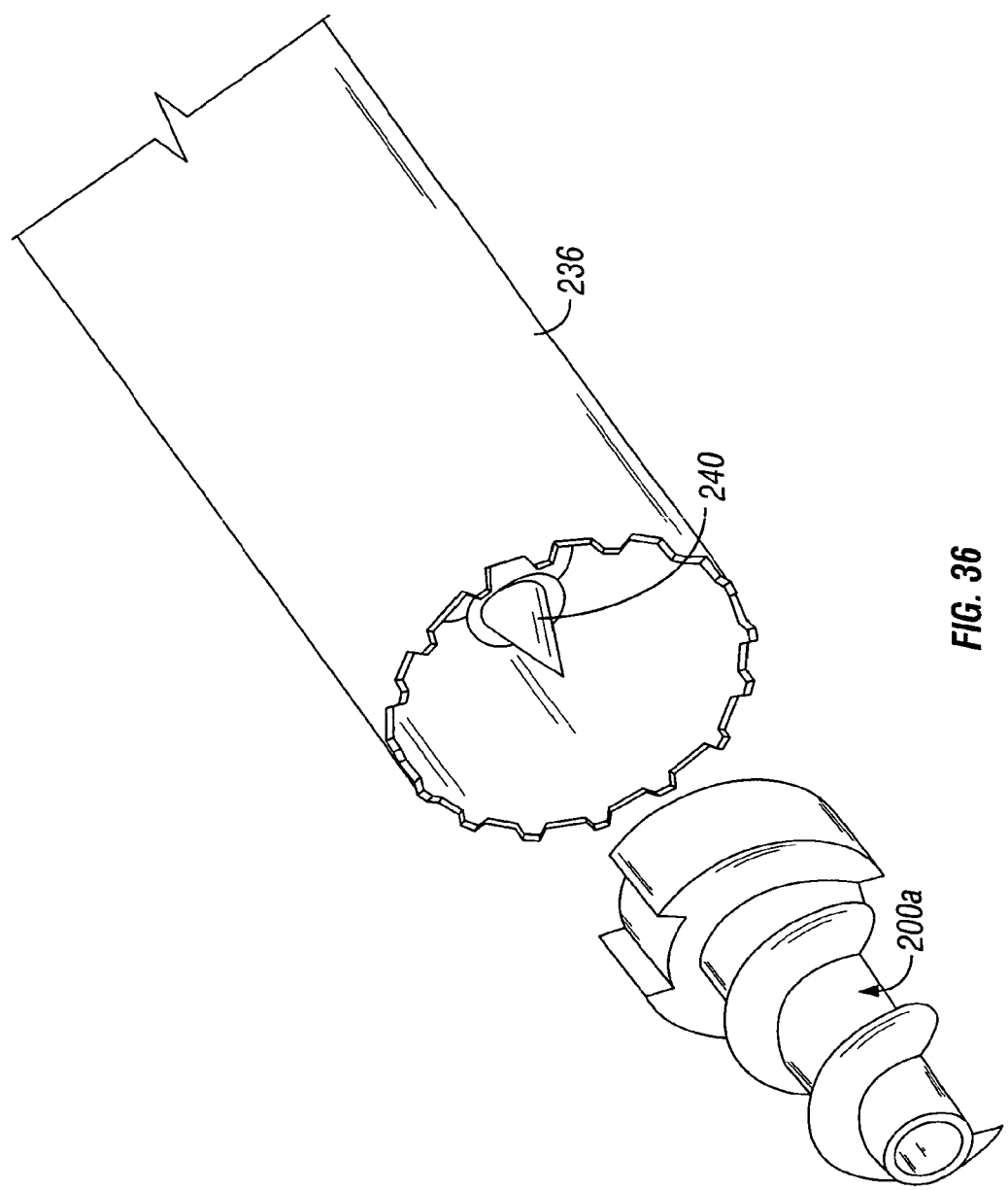

As seen in FIG. 36, cam spiral sub-assembly 248 (see FIG. 34) will drive distal screw fastener 200a an amount sufficient to push distal-most screw fastener 200a beyond tabs 264b of retaining ring 264 (see FIG. 28) and thus releasing distal-most screw fastener 200a from the remainder of the fastener applier.

Desirably, when the trigger of the fastener applier is released, all internal sub-assemblies retract and reorient themselves, thus allowing feed spring 245 to advance the next screw fastener into torque ring 254.

Figure 37:
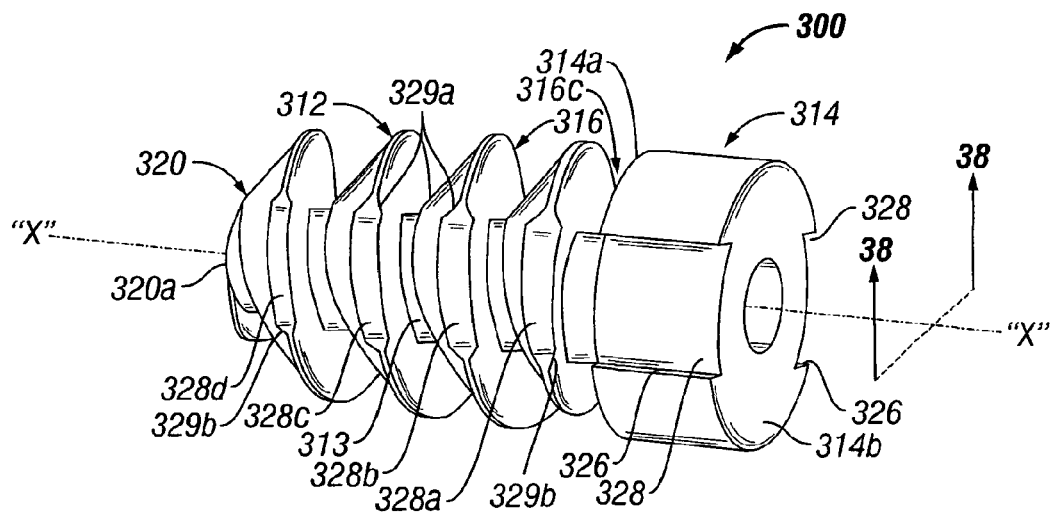
FIG. 37 is a cross-sectional side perspective view of a resorbable screw fastener according to a further embodiment of the present disclosure.
Figure 38:
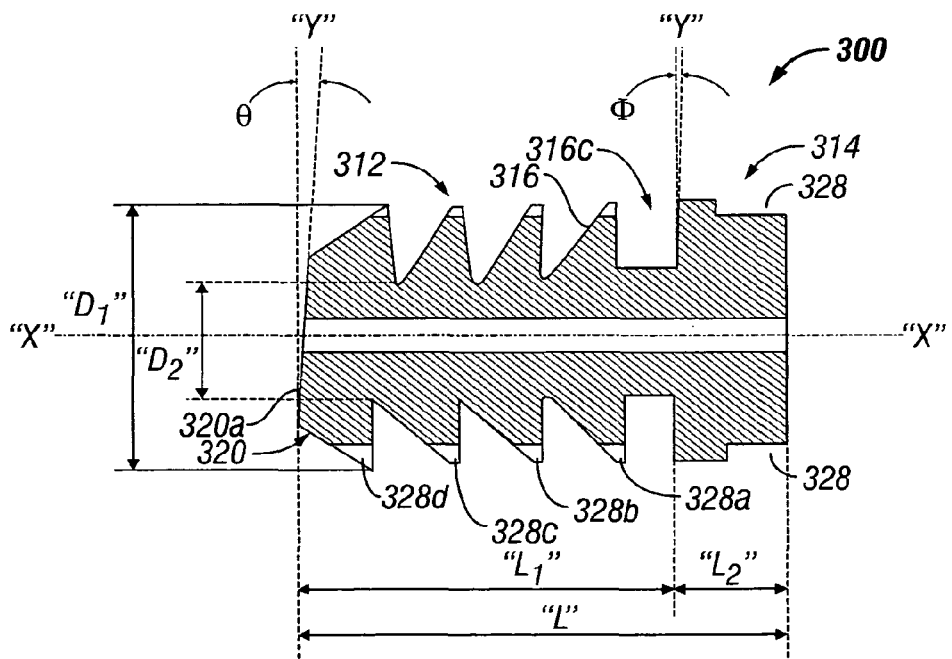
FIG. 38 is a longitudinal cross-sectional view of the resorbable screw fastener of FIG. 37 taken along line 38-38 of FIG. 38.

Turning now to FIGS. 37 and 38, another possible embodiment of the resorbable screw fastener, is shown generally as 300. Screw fastener 300 is similar to screw fastener 10 and will only be discussed in detail to the extent necessary to identify differences in construction and/or operation.

Screw fastener 300 includes a body portion 312 defining a longitudinal axis "X" and a substantially circular head portion 314 disposed on a proximal end of body portion 312. Body portion 312 includes a helical thread 316 extending along a length thereof, and terminates in a distal end 320. In the present embodiment, helical thread 316 is tapered to tangency at the distal end for ease of insertion purposes. The proximal end of helical thread 316 stops before a distal surface of head portion 314 to create gap 316c in which the mesh (not shown) may be received.

Distal end 320 of body portion 312 defines a distal surface 320a which is angled with respect to the "X" axis by an angle Θ. In one embodiment, angle Θ of distal surface 320a is from about 5° to about 15° with respect to an axis "Y" which is orthogonal to the "X" axis. In yet another embodiment, angle Θ is about 9°. Further, body portion 312 includes a center shaft 313 extending along a length thereof. In one embodiment, center shaft 313 is tapered to have a smaller distal end and a larger proximal end in order to increase the ease of insertion of screw fastener 300.

With continued reference to FIGS. 37 and 38, head portion 314 includes driver receiving recesses or structure, in the form of slots 328, formed in an outer radial surface of head portion 314. Slots 328 are configured to transmit torque to screw fastener 300. In one embodiment, a pair of diametrically opposed slots 328 are formed in head portion 314. Each slot 328 may be parallel to the longitudinal "X" axis, and extend through a distal surface 314a and a proximal surface 314b of head portion 314. Slots 328 extend the entire length of screw fastener 300 to define corresponding slots 328a-328d formed in helical thread 316.

In one embodiment, head portion 314 has a low profile, i.e., head portion 314 has a length "L2" which is about 1.5 mm and a distance of about 3.81 mm. Also, body portion 312 may have a length "L1" which is about 5.0 mm. As such, the overall length "L" of screw 300 is about 6.5 mm.

Alternatively or additionally, it is envisioned that a torque transmitting feature may be provided on slots 328, in the form of shoulders 326, the torque transmitting feature allowing for screw fastener 300 to be rotated.

Distal surface 314a may also be angled as shown with respect to the "X" axis by an angle Φ. In one embodiment, angle Φ of distal surface 314a is from about 5° to about 15° with respect to an axis "Y" which is orthogonal to the "X" axis. In yet another embodiment, angle Φ is about 9°. The angle of distal surface 314a is provided to help with the removal of screw fastener 300 in the event that screw fastener 300 needs to be removed from the surgical site.

A space or gap 316c may be provided between a proximal thread run-out and distal surface 314a of head portion 314. Gap 316c allows for the surgical mesh to rest therein. It is envisioned that the pitch of thread 316 may be larger or smaller depending on the particular surgical procedure.

As seen in FIG. 37, each slot 328a-328d includes a radiused distal or leading edge 329a and a radiused proximal or trailing edge 329b. Radiused leading edge 329a and radiused trailing edge 329b help to facilitate insertion of and removal of screw fastener 300 into and from the surgical site.

From the foregoing, it will be appreciated that the screw fastener and fastener applier of the present invention cooperate to securely attach a fastener with high retentive surface area, to tissue, from one direction, through the utilization of a fastener applier having a simpler design. It is also to be appreciated that the present invention may be utilized in a number of applications including ligating tissue, hernia mesh repair, bladder neck suspension, arthroscopic knee surgery, and in conjunction with implant drug delivery systems or procedures involving positioning of surgical or implantable devices in patients.

While several particular forms of the invention have been illustrated and described, it will also be apparent that various modifications can be made without departing form the spirit and scope of the invention.

Thus, it should be understood that various changes in form, detail and application of the present invention may be made without departing form the spirit and scope of the invention.

What is claimed is:

1. A resorbable screw fastener, comprising:
 a body portion defining a longitudinal axis and having a proximal end and a distal end, the distal end having a distal surface extending non-perpendicularly relative to the longitudinal axis, the body portion having a helical thread formed thereon, the helical thread defining a substantially flattened surface formed in an outermost diameter of the helical thread; and
 an unthreaded head portion disposed at the proximal end of the body portion and defining a longitudinal axis, the head portion having a proximal end and a distal end, the distal end of the head portion having a distal surface extending non-perpendicularly relative to the longitudinal axis, the unthreaded head portion including a substantially flattened surface formed in an outermost diameter thereof, wherein the substantially flattened surface of the unthreaded head portion is in radial registration with the substantially flattened surface formed in an outermost diameter of the helical thread, wherein the substantially flattened surface formed in the outermost diameter of the helical thread projects partially radially inward from the outermost diameter of the helical thread.

2. The resorbable screw fastener of claim 1, wherein the head portion further includes a driver receiving structure defining a slot formed in an outer radial side surface of the head portion, the driver receiving structure being configured for receiving both a linear and a rotational force.

3. The resorbable screw fastener of claim 1, wherein said body portion includes a center shaft that is tapered from a narrow distal end to a larger proximal end.

4. The resorbable screw fastener of claim 1, wherein said distal end of the body portion is blunt.

5. The resorbable screw fastener of claim 1, wherein the helical thread includes a proximal surface defining a land that is substantially perpendicular to the longitudinal axis.

6. The resorbable screw fastener of claim 1, wherein a diameter of the head portion is about 3.8 mm.

7. The resorbable screw fastener of claim 1, wherein a height of the head portion is about 1.5 mm.

8. The resorbable screw fastener of claim 1, wherein a length of the body portion is about 5 mm.

9. The resorbable screw fastener of claim 1, further including a central lumen extending through an entire length of the body portion.

10. A resorbable screw fastener, comprising:
a body portion defining a longitudinal axis and having a proximal end and a distal end, the distal end having a distal surface extending non-perpendicularly relative to the longitudinal axis, the body portion having a helical thread formed thereon, at least a portion of the helical thread including a recess formed in an outer radial edge thereof; and
an unthreaded head portion disposed at the proximal end of the body portion and defining a longitudinal axis, the head portion having a proximal end and a distal end, the distal end of the head portion having a distal surface extending non-perpendicularly relative to the longitudinal axis, the unthreaded head portion having a driver receiving structure formed thereon,
wherein the driver receiving structure comprises a recess formed in the outer radial edge of the unthreaded head portion, the recess formed in the unthreaded head portion being substantially in radial registration with the recess formed in the helical thread.

11. The resorbable screw fastener of claim 10, wherein the recess formed in the head portion and the recess formed in the helical thread are planar.

12. The resorbable screw fastener of claim 10, wherein the recess formed in the head portion and the recess formed in the helical thread are flattened.

13. The resorbable screw fastener of claim 10, wherein the recess formed in the head portion and the recess formed in the helical thread are slots.

14. The resorbable screw fastener of claim 10, wherein the recess formed in the head portion is configured to transmit torque.

15. The resorbable screw fastener of claim 10, wherein the recess formed in the head portion and the recess formed in the helical thread are each configured to transmit torque.

16. The resorbable screw fastener of claim 10, wherein the head portion further comprises a plurality of recesses formed in an outer radial edge thereof.

17. The resorbable screw fastener of claim 16, wherein the helical thread further comprises a plurality of recess formed in an outer radial edge thereof.

18. The resorbable screw fastener of claim 17, wherein at least two of the recesses formed in the head portion are substantially in radial registration with corresponding recesses formed in the helical thread.

19. The resorbable screw fastener of claim 10, wherein the resorbable screw fastener is formed from a bioresorbable polymer.

20. The resorbable screw fastener of claim 10, wherein absorption of the resorbable screw fastener is nearly complete at approximately 12 months post implantation.

* * * * *